US010493254B2

(12) United States Patent
Tagliaferri et al.

(10) Patent No.: US 10,493,254 B2
(45) Date of Patent: Dec. 3, 2019

(54) PERMEANT DELIVERY SYSTEM AND METHODS FOR USE THEREOF

(71) Applicant: Nitto Denko Corporation, Tokyo (JP)

(72) Inventors: Frank Tagliaferri, Decatur, GA (US); Alan Smith, Atlanta, GA (US); David Enscore, Alpharetta, GA (US); Gaurav Tolia, Cincinnati, OH (US); Mirek Baudys, Lilburn, GA (US)

(73) Assignee: Nitto Denko Corporation, Tokyo (JP)

( * ) Notice: Subject to any disclaimer, the term of this patent is extended or adjusted under 35 U.S.C. 154(b) by 0 days.

(21) Appl. No.: 15/632,329

(22) Filed: Jun. 24, 2017

(65) Prior Publication Data

US 2019/0117947 A1    Apr. 25, 2019

Related U.S. Application Data

(60) Division of application No. 14/064,868, filed on Oct. 28, 2013, now Pat. No. 10,166,378, which is a
(Continued)

(30) Foreign Application Priority Data

Mar. 31, 2009   (WO) .................. PCTUS2009039045

(51) Int. Cl.
  *A61M 37/00*   (2006.01)
  *A61K 9/70*    (2006.01)
(Continued)

(52) U.S. Cl.
  CPC .......... *A61M 37/00* (2013.01); *A61K 9/7053* (2013.01); *A61K 31/4468* (2013.01);
(Continued)

(58) Field of Classification Search
  CPC .. A61K 31/4468; A61K 31/485; A61K 47/12; A61K 47/183; A61K 47/38;
(Continued)

(56) References Cited

U.S. PATENT DOCUMENTS 5,032,109 A * 7/1991 Sibalis ................. A61K 9/0009
                                                  424/449
5,230,898 A * 7/1993 Horstmann ............ A61K 9/703
                                                  424/443
(Continued)

FOREIGN PATENT DOCUMENTS

EP          1552835          5/2010

OTHER PUBLICATIONS

Office Action dated Feb. 16, 2018 in corresponding Indian Application (Indian Patent Application No. 7661/DENLP/2010).
(Continued)

*Primary Examiner* — Brandy S Lee
(74) *Attorney, Agent, or Firm* — Knobbe, Martens, Olson & Bear, LLP

(57) ABSTRACT

Disclosed are a patch, system, and method for delivery of a permeant composition into a subject via at least one formed pathway through a biological membrane of the subject. The patch comprises a matrix, at least one hydrophilic permeant disposed within the matrix, wherein at least a portion of the permeant can dissolve in biological moisture received from the subject, and at least one permeability enhancer disposed within the matrix. Also disclosed are systems and methods for delivery of a permeant composition into a subject via at least one formed pathway through a skin layer of the subject.

24 Claims, 10 Drawing Sheets

Related U.S. Application Data continuation of application No. 12/893,477, filed on Sep. 29, 2010, now Pat. No. 9,498,609, which is a continuation of application No. PCT/US2009/039045, filed on Mar. 31, 2009.

(60) Provisional application No. 61/040,744, filed on Mar. 31, 2008, provisional application No. 61/133,101, filed on Jun. 25, 2008.

(51) Int. Cl.
| | |
|---|---|
| *A61K 31/4468* | (2006.01) |
| *A61K 31/485* | (2006.01) |
| *A61K 47/12* | (2006.01) |
| *A61K 47/18* | (2017.01) |
| *A61K 47/38* | (2006.01) |
| *A61P 5/50* | (2006.01) |
| *A61P 23/02* | (2006.01) |

(52) U.S. Cl.
CPC ............ *A61K 31/485* (2013.01); *A61K 47/12* (2013.01); *A61K 47/183* (2013.01); *A61K 47/38* (2013.01); *A61P 5/50* (2018.01); *A61P 23/02* (2018.01)

(58) Field of Classification Search
CPC ...... A61K 9/7053; A61M 37/00; A61P 23/02; A61P 5/50
See application file for complete search history.

(56) References Cited

U.S. PATENT DOCUMENTS

| | | | |
|---|---|---|---|
| 2005/0074487 | A1 | 4/2005 | Hsu |
| 2006/0013865 | A1 | 1/2006 | Ito |
| 2006/0233871 | A1* | 10/2006 | Stern .................. A61K 9/0021 424/449 |
| 2007/0031495 | A1* | 2/2007 | Eppstein .............. A61K 9/7053 424/473 |
| 2007/0083186 | A1* | 4/2007 | Carter .................. A61N 1/044 604/501 |

OTHER PUBLICATIONS

First Office Action in corresponding application CN 201510333806.7.

First Office Action in corresponding application CN 201510333806.7 (English Summary).

* cited by examiner

PERMEANT DELIVERY SYSTEM AND METHODS FOR USE THEREOF

PRIORITY CLAIM

This application is a divisional of U.S. patent application Ser. No. 14/064,868 filed Oct. 28, 2013 which is a continuation of U.S. patent application Ser. No. 12/893,477 filed Sep. 29, 2010 which is a continuation of PCT/US2009/039045 filed Mar. 31, 2009 which claims the benefit of U.S. Provisional Patent Application Ser. No. 61/040,744 filed Mar. 31, 2008, the contents of which are hereby incorporated by reference in its entirety. This application also claims the benefit of U.S. Provisional Patent Application Ser. No. 61/133,101 filed Jun. 25, 2008, the contents of which are hereby incorporated by reference in its entirety.

FIELD OF THE INVENTION

The present invention relates generally to the field of transdermal permeant delivery and more specifically to devices, systems and methods for using the same.

BACKGROUND OF THE INVENTION

Transdermal drug delivery systems have been marketed for a variety of therapeutic indications over the past 20 years. Typically, transdermal delivery systems are fabricated as multilayered polymeric laminates in which a drug reservoir or a drug-polymer matrix is sandwiched between two polymeric layers: an outer impervious backing layer that creates an occlusive environment and prevents the loss of drug through the backing surface and an inner polymeric layer that functions as an adhesive and/or rate-controlling membrane. In the case of a drug reservoir design, the reservoir is sandwiched between the backing and a rate controlling membrane. The drug releases only through the rate-controlling membrane, which can be microporous or nonporous. In the drug reservoir compartment, the drug can be in the form of a solution, suspension, or gel or dispersed in a solid polymer matrix. On the outer surface of the polymeric membrane a thin layer of drug-compatible, hypoallergenic adhesive polymer may be applied.

In the case of the drug matrix design, there are two types, the drug-in-adhesive system and the matrix dispersion system. In the drug-in-adhesive system, the drug reservoir is formed by dispersing the drug in an adhesive polymer and then spreading the medicated polymer adhesive by solvent casting or by melting the adhesive (in the case of hot-melt adhesives) onto an impervious backing layer. On top of the reservoir, layers of unmedicated adhesive polymer are applied. In the case of the matrix dispersion system, the drug is dispersed homogeneously in a hydrophilic or lipophilic polymer matrix and fixed onto a drug-impermeable backing layer by solvent casting or extrusion. Instead of applying the adhesive on the face of the drug reservoir, it is applied to form a peripheral adhesive.

Most conventional transdermal products contain small molecule drugs (<500 Daltons) that are lipophilic in nature, allowing them to dissolve into and diffuse through the lipid bilayers of the outer layer of the skin, the stratum corneum. Most transdermal products contain the lipophilic base form of the drug, not the hydrophilic or water soluble salt form. Transdermal delivery is typically limited to small molecules to allow a sufficient flux into the body across a reasonably sized patch area. To increase transdermal flux, chemical permeation enhancers have been added to transdermal formulations. However, use of chemical permeation enhancers has not been successful in achieving a sufficient flux of a hydrophilic or water soluble drug or any molecule larger than 1000 Daltons to reach therapeutic levels. Accordingly, there is a need in the art for improved methods, systems and devices for achieving transdermal delivery of permeants to a subject at therapeutic delivery rates.

SUMMARY OF THE INVENTION

The present invention provides devices, systems and methods for delivery of permeants through a biological membrane of a subject.

In a first aspect, the present invention is a patch which contains a matrix, at least one hydrophilic permeant and at least one permeability enhancer disposed within the matrix, where at least a portion of the hydrophilic permeant can dissolve in biological moisture received from the subject.

In one embodiment of the present invention, the hydrophilic permeant is a bioactive agent. In a particular embodiment, the hydrophilic permeant is a protein. In another particular embodiment, the hydrophilic permeant is a small molecule. In one embodiment, the hydrophilic permeant is selected from exenatide, fentanyl citrate, hydromorphone or insulin.

In another embodiment of the present invention, the permeability enhancer is a pH control agent. In a particular embodiment, the permeability enhancer is selected from disodium citrate, succinic acid or tris.

In yet another embodiment of the present invention, the matrix is a polymer matrix. In one embodiment, the polymer matrix contains a single polymer. In a particular embodiment, the polymer is selected from a water insoluble polymer or water soluble polymer. Ethylene vinyl acetate and ethyl cellulose are typical water insoluble polymers. Polyvinyl alcohol is a typical water soluble polymer.

In a still further embodiment of the present invention, the polymer matrix contains two or more polymers. In one embodiment, the two or more polymers are selected from water insoluble polymers, water soluble polymers or combinations thereof. In a particular embodiment, the polymer matrix contains ethylene vinyl acetate and ethyl cellulose. In another particular embodiment, the polymer matrix contains ethylene vinyl acetate and polyvinyl alcohol.

In another embodiment of the invention, the hydrophilic permeant is delivered to the subject for an administration period ranging from about 5 minutes to about 7 days. In one embodiment, the hydrophilic permeant is delivered to the subject for an administrative period of about 7 days. In another embodiment, the hydrophilic permeant is delivered to the subject for an administrative period of about 3 days. In a further embodiment, the hydrophilic permeant is delivered to the subject for an administrative period ranging from about 12 to about 36 hours. In yet another embodiment, the hydrophilic permeant is delivered to the subject for an administrative period of about 24 hours.

In a further embodiment of the present invention, the patch also includes a solubility control agent. In one embodiment, the solubility control agent is a salt. In a particular embodiment, the solubility control agent is selected from sodium chloride or ammonium sulfate. In a specific embodiment, the present invention is a patch for delivery of exenatide through a biological membrane of a subject, wherein the patch includes an polymer matrix containing exenatide and at least one permeability enhancer, wherein at least a portion of the exenatide dissolves in biological moisture received from the subject. In a particular embodiment, the permeability enhancer is a pH control agent. In one embodiment, the pH control agent is succinic acid. In a further particular embodiment, the polymer matrix contains ethylene vinyl acetate and ethyl cellulose. In a particular embodiment, exenatide is delivered to the subject for an administrative period of from about 5 hours to about 7 days. In one embodiment, exenatide is delivered to a subject of an administrative period of about 24 hours, about 3 days or about 7 days.

In a further specific embodiment, the present invention is a patch for delivery of insulin through a biological membrane of a subject, wherein the patch includes an polymer matrix containing insulin and at least one permeability enhancer, wherein at least a portion of the insulin dissolves in biological moisture received from the subject. In a particular embodiment, the permeability enhancer is a pH control agent. In a specific embodiment, the pH control agent is tris. In another particular embodiment, the polymer matrix contains ethylene vinyl acetate and polyvinyl alcohol. In a particular embodiment, insulin is delivered to the subject for an administrative period of from about 5 hours to about 7 days. In one embodiment, insulin is delivered to a subject of an administrative period of about 24 hours, about 3 days or about 7 days.

According to a second aspect, the present invention is a patch which contains exenatide and at least one permeability enhancer. The permeability enhancer can be any permeability enhancer described above with respect to the first aspect of the invention. In a particular embodiment, the permeability enhancer is a pH control agent. In one embodiment, the patch contains a polymer matrix, wherein the polymer may be any polymer described above with respect to the first aspect of the invention. In another embodiment, the patch contains a permeant reservoir. In yet another embodiment, the patch further comprises a solubility control agent, wherein the solubility control agent may be any solubility control agent described above with respect to the first aspect of the invention. In a still further embodiment, the exenatide is delivered to the subject for an administration period, wherein the administration period may be any period described above with respect to the first aspect of the invention.

According to a third aspect, the present invention is a patch which contains at least one permeant and at least one pH control agent selected from succinic acid or tris. The permeant may be any permeant described above with respect to the first aspect of the invention. In another embodiment, the patch contains a polymer matrix, wherein the polymer may be any polymer described above with respect to the first aspect of the invention. In a still further embodiment, the patch contains a permeant reservoir. In a still further embodiment, the permeant is delivered to the subject for a administration period, wherein the administration period may be any period described above with respect to the first aspect of the invention.

In one specific embodiment, the present invention is a patch which contains a permeant reservoir, exenatide and at least one pH control agent selected from succinic acid or tris.

In another specific embodiment, the present invention is a patch which contains a permeant reservoir, insulin and a pH control agent selected from succinic acid or tris.

According to a fourth aspect, the present invention is a system for delivering a permeant through a biological membrane of a subject, which system includes both a porator and a patch, wherein the patch contains a matrix and at least one hydrophilic permeant and at least one permeability enhancer disposed within the matrix, wherein at least a portion of the hydrophilic permeant can dissolve in biological moisture provided by the subject through one or more micropores formed by said porator. In one embodiment, the porator is a thermal porator. In another embodiment, the porator is selected from a mechanical porator, a laser porator or a hydraulic porator.

The various embodiments described above with respect to first aspect of the present invention are also applicable to the fourth aspect of the invention, including the hydrophilic permeant, the permeability enhancer, the matrix including the various polymer components, the additional solubility control agent and the period of administration.

In a specific embodiment, the present invention is a system for delivering exenatide through a biological membrane of a subject including a porator and patch, wherein the patch includes an polymer matrix containing exenatide and at least one permeability enhancer, wherein at least a portion of the exenatide dissolves in biological moisture provided by the subject and is delivered to the subject over an administrative period ranging from about 5 minutes to about 7 days. In a particular embodiment, the porator is a thermal porator. In another particular embodiment, the permeability enhancer is a pH control agent. In one embodiment, the pH control agent is succinic acid. In another particular embodiment, the polymer matrix contains ethylene vinyl acetate and ethyl cellulose. In another particular embodiment, exenatide is delivered to the subject over an administration period selected from about 24 hours, about 3 days or about 7 days.

In another specific embodiment, the present invention is a system for delivering insulin through a biological membrane of a subject including a porator and patch, wherein the patch includes an polymer matrix containing insulin and at least one permeability enhancer, wherein at least a portion of the insulin dissolves in biological moisture provided by the subject. In a particular embodiment, the porator is a thermal porator. In another particular embodiment, the permeability enhancer is a pH control agent. In one embodiment, the pH control agent is tris. In another particular embodiment, the polymer matrix contains ethylene vinyl acetate and polyvinyl alcohol. In another particular embodiment, insulin is delivered to the subject over an administration period selected from about 24 hours, about 3 days or about 7 days.

According to a fifth aspect, the present invention is a system for delivering exenatide through a biological membrane of a subject, which system includes both a porator and a patch, wherein the patch contains exenatide and at least one permeability enhancer. The porator can be any porators described above with respect to the fourth aspect of the invention. In a particular embodiment, the porator is a thermal porator. selected from a mechanical porator, a laser porator or a hydraulic porator.

The various embodiments described above with respect to second aspect of the present invention are also applicable to the fifth aspect of the invention, including the permeability enhancer, the matrix including the various polymer components, the additional solubility control agent and the period of administration. In one embodiment, the patch contains a permeant reservoir.

According to a sixth aspect, the present invention is a system for delivering exenatide through a biological membrane of a subject, which system includes both a porator and a patch, wherein the patch contains least one permeant and at least one pH control agent selected from succinic acid or tris.

The various embodiments described above with respect to third aspect of the present invention are also applicable to the sixth aspect of the invention, including the permeability enhancer, the matrix including the various polymer components, the additional solubility control agent and the period of administration. In one embodiment, the patch contains a permeant reservoir.

According to a seventh aspect, the present invention is a method for delivering a permeant through a biological membrane of a subject comprising the steps of forming one or more micropores in the biological membrane and placing a patch in physical contact with the one or more micropores to allow for delivery of the permeant, wherein the patch contains a polymer matrix and at least one hydrophilic permeant and at least one permeability enhancer disposed within the matrix, wherein at least a portion of the hydrophilic permeant can dissolve in biological moisture provided by the subject through one or more micropores formed by said porator. In one embodiment, the one or more micropores are formed by a thermal poration device. In another embodiment, the one or more micropores are formed by a device selected from a mechanical puncture device, a laser ablation device or a hydraulic pressure device. In a particular embodiment, the micropores are formed by a heat conducting element placed in substantial physical contact with a biological membrane to deliver sufficient energy to the biological membrane to thermally ablate the biological membrane.

The various embodiments described above with respect to first, second and third aspects of the present invention are also applicable to the seventh aspect of the invention, including the permeant, the permeability enhancer, the matrix including the various polymer components, the permeant reservoir, the additional solubility control agent and the period of administration.

Additional aspects of the invention will be set forth, in part, in the detailed description, figures and any claims which follow, and in part will be derived from the detailed description, or can be learned by practice of the invention. It is to be understood that both the foregoing general description and the following detailed description are exemplary and explanatory only and are not restrictive of the invention as disclosed.

BRIEF DESCRIPTION OF THE FIGURES

The accompanying drawings, which are incorporated in and constitute a part of this specification, illustrate certain aspects of the instant invention and together with the description, serve to explain, without limitation, the principles of the invention.

DETAILED DESCRIPTION OF THE INVENTION

Figure 1:
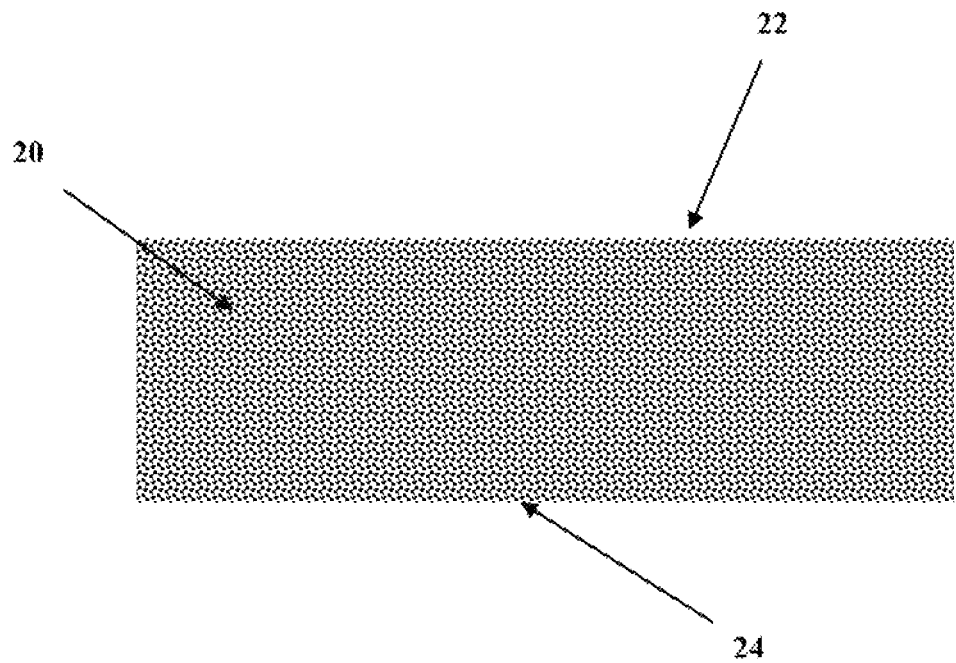
FIG. 1 illustrates a side view of a permeant delivery patch according to one aspect of the present invention.

The present invention can be understood more readily by reference to the following detailed description, examples, and claims, and their previous and following description.

Before the present compositions, devices, systems, and/or methods are disclosed and described, it is to be understood that this invention is not limited to the specific articles, devices, systems, and/or methods disclosed unless otherwise specified. It is also to be understood that the terminology used herein is for the purpose of describing particular aspects only and is not intended to be limiting.

The following description of the invention is provided as an enabling teaching of the invention in its best, currently known embodiment. Those skilled in the relevant art will recognize that many changes can be made to the embodiments described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a patch comprising a "bioactive agent" includes aspects having two or more bioactive agents unless the context clearly indicates otherwise. Ranges can be expressed herein as from "about" one particular value, and/or to "about" another particular value. When such a range is expressed, another aspect includes from the one particular value and/or to the other particular value. Similarly, when values are expressed as approximations, by use of the antecedent "approximately" or "about," it will be understood that the particular value forms another aspect. It should also be understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

As used herein, a "weight percent" or "percent by weight" of a component, unless specifically stated to the contrary, is based on the total weight of the formulation or composition in which the component is included. As used herein, the term or phrase "effective," "effective amount," or "conditions effective to" refers to such amount or condition that is capable of performing the function or property for which an effective amount is expressed. As will be pointed out below, the exact amount or particular condition required will vary from one embodiment to another, depending on recognized variables such as the materials employed and the processing conditions observed. Thus, it is not always possible to specify an exact "effective amount" or "condition effective to." However, it should be understood that an appropriate effective amount or effective condition will be readily determined by one of ordinary skill in the art using only routine experimentation. As used herein, a "therapeutic amount" or a "therapeutically effective amount" of a permeant refers to an amount of permeant capable of providing a desired result. The desired result can be expected, unexpected, or even an unintended consequence of the administration of the permeant.

As used herein, the term "patch", in non-limiting examples, may include traditional drug reservoir or drug matrix patches or any other type of patch suitable for use in transdermal drug delivery techniques. In one embodiment of a drug reservoir design, the reservoir may be sandwiched between a backing and a rate controlling membrane. The drug releases only through the rate-controlling membrane, which can be microporous or nonporous. In the drug reservoir compartment, the drug can be in a form such as, but not limited to, a solution, suspension, or gel or dispersed in a solid framework. On the outer surface of the membrane a thin layer of drug-compatible, hypoallergenic adhesive polymer may be optionally applied. In one embodiment of the drug matrix design, both commonly known types, the drug-in-adhesive system and the matrix dispersion system are to be included. In one embodiment of the drug-in-adhesive system, the drug reservoir may be formed by dispersing the drug in an adhesive polymer and then spreading the medicated polymer adhesive by solvent casting or by melting the adhesive (in the case of hot-melt adhesives) onto an impervious backing layer. On top of the reservoir, layers of unmedicated adhesive polymer may be applied. In one embodiment of the matrix dispersion system, the drug is dispersed homogeneously in a hydrophilic or lipophilic polymer matrix and fixed onto a drug-impermeable backing layer. In another embodiment, instead of applying the adhesive on the face of the drug reservoir, it is applied to form a peripheral adhesive. All forms of patches that can be placed on the skin, including the above traditional drug reservoir and drug matrix style patches, are to be included as embodiments of the present invention.

As used herein, the term "hydrophilic permeant" refers to a permeant having an affinity for moisture. In one aspect, the moisture can be present in or provided by subcutaneous fluid. The subcutaneous fluid can be intracellular and/or extracellular fluid. In one aspect, a hydrophilic permeant can be at least substantially water-soluble such that once contacted with a water or moisture source, such as subcutaneous fluid, the hydrophilic permeant at least substantially dissolves in the subcutaneous fluid. In another aspect, the hydrophilic permeant may not substantially dissolve in the subcutaneous fluid but rather may form a suspension of particulate hydrophilic permeant in the subcutaneous fluid. As further used herein, hydrophilic permeant composition can include one or more hydrophilic permeants as described herein.

As used herein, a "subcutaneous fluid" or "biological moisture" can include, without limitation, moisture, plasma, blood, one or more proteins, interstitial fluid, skin tissue fluid, fluid from any of the layers of the skin, perspiration, serum, lymphatic fluid, and/or any combination of two or more thereof. In one aspect, a subcutaneous fluid according to the instant invention is a moisture source that includes water. As used herein, the term "non-biodegradable" refers to a material, compound or composition, which, does not substantially degrade, dissolve, or erode when contacted by subcutaneous fluid. In one aspect, a non-biodegradable material, compound or composition can be a substantially water-insoluble material, compound, or composition. As used herein, the term "permeant utilization" refers to the percentage of the initial permeant content disposed within a permeant delivery patch that is transdermally delivered from patch into a subject during a predetermined permeant administration period.

As used herein, a "subject" refers to any living organism having at least one biological membrane through which fluid can be obtained. In one aspect, an exemplary biological membrane can be at least one skin layer through which subcutaneous fluid can be obtained. For example, in one aspect a subject can be a plant. Alternatively, in another aspect, the subject can be an animal. In one aspect the animal can be mammalian. In an alternative aspect the animal can be non-mammalian. The animal can also be a cold-blooded animal, such as a fish, a reptile, or an amphibian. Alternatively, the animal can be a warm-blooded animal, such as a human, a farm animal, a domestic animal, or even a laboratory animal. Accordingly, it should be understood that the present invention is not limited to its use in connection with any one particular subject or group of subjects. As used herein, a "biological membrane" includes an enclosing or separating layer that acts as a barrier within or around a cell. In some aspects it can be a lipid bilayer comprised of lipid-class molecules and occasional intertwined proteins. Biological membranes as used herein can also define enclosed spaces or compartments in which cells can maintain a chemical or biochemical environment that differs from the environment outside of the space or compartment. In some aspects, the biological membrane can be a selectively-permeable structure, whereby the size, charge, and other chemical properties of the atoms and molecules attempting to cross it will determine whether they are capable of doing so. In one aspect, the biological membrane can be a mucosal membrane. Exemplary mucosal membranes can include, but are not limited to, oral, gingival, gastrointestinal, cervical, vaginal, intrarectal, intranasal, buccal, and ocular membranes. In another aspect, the biological membrane can be a skin layer.

As used herein, a "skin layer" can be any one or more epidermal layers of a subject. For example, in one aspect, a skin layer includes the outermost layer of the skin, i.e., the stratum corneum. In an alternative aspect, a skin layer can include one or more layers of the epidermis beneath the stratum corneum, commonly identified as stratum granulosum, stratum spinosum (stratum malpighii), and stratum basale (stratum germinativum) layers. It will be appreciated by one of ordinary skill in the art that there is essentially little or no resistance to transport or to absorption of a permeant through the layers of the epidermis underneath the stratum corneum. Therefore, in one aspect of the present invention, an at least one formed pathway in a skin layer of a subject is a pathway in the stratum corneum layer of a subject.

As used herein, "enhancer," "chemical enhancer", "penetration enhancer," "permeation enhancer," "permeability enhancer", and the like include all enhancers that increase the flux of a permeant, analyte, or other molecule across the biological membrane, or within the tissue fluid. All cell envelope disordering compounds and solvents and any other chemical enhancement agents are intended to be included. Additionally, pH control agents, solubility control agents (including ionic strength control agents, salting-out agents, and water soluble polymers) and fillers are intended to be included. Additionally, all active force enhancer technologies including, but not limited to, the application of sonic energy, mechanical suction, pressure, or local deformation of the tissues, sonophoresis, iontophoresis or electroporation are included. In some cases, the hydrophilic permeant can also act concurrently (with its role as permeant) or separately as a permeability enhancer. One or more enhancer technologies may be combined sequentially or simultaneously. For example, a chemical enhancer may first be applied to permealize the capillary wall and then an iontophoretic or sonic energy field may be applied to actively drive a permeant into those tissues surrounding and comprising the capillary bed. As used herein, "transdermal" or "percutaneous" includes the passage of a permeant into and through one or more skin layers to achieve effective therapeutic blood levels or local tissue levels of a permeant.

As used herein, a "formed opening", "artificial opening", or "micropore" means any physical breach of the biological membrane of a suitable size for delivering or extracting fluid there through. "Formed opening," "artificial opening," "micropore," thus refers to a small hole, opening or crevice created to a desired depth in or through a biological membrane. In one embodiment, the term micropore refers to the result of any skin abrading technology that results in biological fluid production to the skin surface. In one embodiment, the opening may be formed via the conduction of thermal energy as described in U.S. Pat. Nos. 5,885,211 and 7,141,034, the teachings of which are incorporated herein by reference, or through a mechanical process, through a pyrotechnic process, or through use of radio frequency ablation. In some aspects, the size of the hole or pore can for example be approximately 1-1000, 5-700, 10-500, 50-300, 100-250, 50-100, or 70-90 microns in diameter. The hole or pore may be any shape, for example, cylinder, slit, hole, square, trough, crater, and the like. It is to be understood that the term micropore is used in the singular form for simplicity, but that the devices, systems, and methods may form an array of multiple openings or pores. As used herein, "poration", "microporation", or any such similar term means the formation of a small hole or crevice (subsequently also referred to as a "micropore") in or through the tissue or biological membrane, such as skin or mucous membrane, or the outer layer of an organism to lessen the barrier properties of this biological membrane for the passage of at least one permeant from one side of the biological membrane to the other for select purposes. Preferably the hole or "micropore" so formed is approximately 1-1000 microns in diameter and extends into the biological membrane sufficiently to break the barrier properties of the stratum corneum without adversely affecting the underlying tissues. In other embodiments, the hole or micropore so formed is approximately 1-1000, 5-700, 10-500, 50-300, 100-250, 50-100, or 70-90 microns in diameter. It is to be understood that the term "micropore" is used in the singular form for simplicity, but that the device of the present invention may form multiple artificial openings. Poration could reduce the barrier properties of a biological membrane into the body for selected purposes, or for certain medical or surgical procedures. The microporation process referred to herein is distinguished from the openings formed by electroporation principally by the typical minimum dimensions of the micropores which are usually no smaller than about 1 micron across and usually at least about 1 micron in depth, whereas the openings formed with electroporation are typically only a few nanometers in any dimension. Nevertheless, electroporation is useful to facilitate uptake of selected permeants by the targeted tissues beneath the outer layers of an organism after the permeant has passed through the micropores into these deeper layers of tissue. For the purposes of this application, "poration" and "microporation" are used interchangeably.

A "microporator" or "porator" is a component for a microporation device capable of microporation. Examples of a microporator or porator include, but are not limited to: thermal poration devices including devices with one or more filaments capable of conductively delivering thermal energy via direct contact to a biological membrane to cause the ablation of some portion of the membrane deep enough to form a micropore, heat conducting elements placed in substantial physical contact with a biological membrane to deliver sufficient energy to the biological membrane to thermally ablate said biological membrane, and optically heated topical dye/absorber layers; mechanical ablation devices including electromechanical actuators, microlancets, and an array of solid or hollow microneedles or lancets; radiofrequency ablators, sonic energy ablators; laser ablation systems; hydraulic puncture devices including high-pressure fluid jet puncturers; techniques using physical abrasion of the skin surface; dermal ballistic delivery devices; and the like. A Thin Film Tissue Interface as described in U.S. Pat. No. 7,141,034, the entirety of which is incorporated by reference, is a further example of a porator. As used herein, "microporator" and "porator" are used interchangeably. "Thin Film Tissue Interface" or "TFTI" is used to describe a device that creates micropores using thermal energy produced by the passage of electrical current through resistive elements and methods of manufacturing and functional operation of the TFTI devices. TFTI devices create one or more micropores on a wide range of biological membranes. TFTIs have applications that include thermal microporation of human skin for the enhancement of analyte monitoring and delivery of permeants such as a therapeutic drug or a tattoo dye. TFTIs are characterized by their ability to rapidly and efficiently create a pattern or array of micropores on the surface of a biological membrane. The pattern may be any geometric spacing of micropores with various possible pore densities. In one embodiment, the pore density is as high as one pore every 0.2 square mm and pore densities may cover a total porated area ranging from a few square millimeters to greater than several hundred square centimeters, including 0.005-800, 0.01-500, 0.1-500, 1-300, 10-200, 25-100, and 50-75 square centimeters. TFTI devices are designed to be thin, flexible, conformable structures that may form an interface between the biological membrane and a controller.

Alternatively, the TFTI may be integrated with the controller itself and this integrated device may contact the biological membrane. The controller portion supplies each poration element or electrode or other active component such as a piezo-transducer in the TFTI with the required electrical signal to effect the poration or other function of the TFTI such as, but not limited to, iontophoresis, sonophoresis, electroporation, or impedance measurement of the contacted tissue. TFTIs are flexible and may be able to conform to the shape of the targeted biological membranes. The TFTIs are fabricated to be very thin, light in weight, and may be used separately from a patch or in an integrated fashion and are also connected to the controller or current source through an umbilical cable to allow a more user friendly configuration. When one or more controllable active additional flux enhancement features are incorporated into the TFTI, such as, but not limited to, pressure modulation, mechanical manipulation, iontophoresis, electro-osmosis, sonophoresis or electroporation, the activation of this additional flux control feature could be controlled by the remote controller module either in a preprogrammed fashion, a user controlled fashion via inputs to the controller, or in an automatic, closed loop fashion wherein the rate of infusion of a permeant is modulated as a function of the measured level of a selected analyte within or other measurable property of the organism. The other measurable property could include heart rate, blood pressure, temperature, respiration, and skin surface conductivity. For example, in one embodiment, it is useful to control the rate of insulin infusion based on the real-time measurement of glucose concentrations in the interstitial fluid or serum of an organism. In another embodiment, it is desirable with some therapeutic compounds, particularly those with narrower therapeutic windows defining what an effective drug level is versus when the negative side effects become too intolerable, to modulate the infusion rates based on the measurable levels of this compound within the organism, thereby allowing a very accurate, and self adaptive method for achieving and maintaining the drug concentration within a desired therapeutic window regardless of patient body mass or metabolism. In the design and manufacture of the TFTI, many of the electrically conductive traces comprising the TFTI could be used to serve multiple functions. For example, the traces used to deliver the short pulses of current to the resistive poration elements to induce the thermal cycling, could also be used for either closed loop feedback control of the microporation or to incorporate enhancement as electrodes for an iontophoretic or electroporation process, carried out after the micropores have been formed.

As used herein, "iontophoresis" refers to the application of an external electric field to the tissue surface through the use of two or more electrodes and delivery of an ionized form of drug or an un-ionized drug carried with the water flux associated with ion transport (electro-osmosis) into the tissue or the similar extraction of a biological fluid or analyte.

As used herein, "electroporation" refers to the creation through electric current flow of openings in cell walls that are orders of magnitude smaller than micropores. The openings formed with electroporation are typically only a few nanometers, for example 1-10 nanometers, in any dimension. In one example, electroporation is useful to facilitate cellular uptake of selected permeants by the targeted tissues beneath the outer layers of an organism after the permeant has passed through the micropores into these deeper layers of tissue.

As used herein, "sonophoresis" or "sonification" refers to sonic energy, which may include frequencies normally described as ultrasonic, generated by vibrating a piezoelectric crystal or other electromechanical element by passing an alternating current through the material. The use of sonic energy to increase the permeability of the skin to drug molecules has been termed sonophoresis or phonophoresis.

The present invention is based, in part, upon new approaches to transdermal delivery that have been developed through increasing the permeability of a biological membrane. According to some aspects, the permeability can be achieved by physically altering the membrane via the formation of artificial openings or pathways through at least one layer of the membrane. These openings can provide fluid communication or access through the membrane. For example, where the biological membrane is the stratum corneum skin layer, the formed openings can provide access or fluid communication to the hydrated, living layers of the epidermal and dermal skin tissues beneath the stratum corneum layer. To that end, these openings, or micropores, can be viewed as aqueous channels or formed pathways, through which not only permeant can diffuse, but fluid can be pumped, micro-particles can be delivered, or fluid from within the subject can exude to the surface of the skin. By utilizing the bi-directional properties of fluid flow and micropores of this type the present invention provides, in one aspect, improved devices, systems and methods of transdermal permeant delivery as described in detail below.

According to aspects of the invention, a patch or a system including the patch plus a porator is provided for causing flux of a bioactive agent into a subject via at least one formed pathway through a biological membrane of the subject. The patch includes a matrix. The matrix has a surface adapted for contacting a biological membrane and the matrix is further adapted to absorb or otherwise receive biological moisture from at least one formed pathway through the biological membrane. A permeant composition is disposed within the matrix. The permeant composition includes an undissolved hydrophilic permeant, where said hydrophilic permeant may include at least one bioactive agent, and further includes at least one permeability enhancer like a pH control agent. In one embodiment, the hydrophilic permeant of the permeant composition is delivered into the subject. In another embodiment, both the hydrophilic permeant and the permeability enhancer of the permeant composition are delivered into the subject. In some aspects, the bioactive agent can also provide the functionality of the at least one permeability enhancer.

In one embodiment, the permeant composition can come in contact with biological moisture, such as subcutaneous fluid, when the bottom surface of the patch is positioned in fluid communication with the at least one formed pathway through the biological membrane of a subject. In another embodiment, at least a portion of the undissolved hydrophilic permeant, and in some instances, at least a portion of the permeability enhancer as well, can dissolve in or form a suspension in the contacted biological moisture from the subject. Not to be limited by this explanation, in one embodiment it is believed that once an effective amount of moisture has come into contact with the permeant composition in the matrix, the fluid subsequently provides a diffusion path for delivering at least a portion of the permeant back through the biological membrane into the subject. In another aspect and without limitation, the permeant composition can have an affinity for subcutaneous fluid such that at least a portion of the permeant composition can draw an effective amount of subcutaneous fluid from the subject when the bottom surface of the patch is positioned in fluid communication with the at least one formed pathway through the skin layer of a subject.

In one embodiment, the matrix has a surface adapted for contacting a biological membrane and is further adapted to absorb or otherwise receive biological moisture from at least one formed pathway through the biological membrane when the patch is positioned in fluid communication with at least one formed pathway. The matrix can include at least one polymer and can include two or more polymers. The polymer or polymers may be water soluble or water insoluble polymers. A single matrix may include both water soluble and water insoluble polymers. Non-limiting examples of water soluble polymers include polyethylene glycol (PEG or PEO or POE), polyvinyl alcohol (PVA or PVOH), and polyvinylpyrrolidone (PVP). Non-limiting examples of water insoluble polymers include ethylene vinyl acetate (EVA) and ethyl cellulose (EC). The matrix material can, in an exemplary non-limiting aspect, account for approximately 1 weight % to approximately 99 weight % of the patch, including additional amounts of about 25 weight %, about 30 weight %, about 35 weight %, about 40 weight %, about 45 weight %, about 50 weight %, about 55 weight %, about 60 weight %, about 65 weight %, about 70 weight %, about 75 weight % and about 80 weight % of the patch. Additionally, the matrix material can account for any amount in any range of weight percentages derived from these values. For example, in exemplary non-limiting aspects, the matrix material can be in the range of from about 1 to about 60 weight % of the patch, about 20 to about 60 weight % of the patch, about 20 to about 40 weight % of the patch, or even about 1 to about 40 weight % of the patch.

According to aspects of the invention, the matrix can include a water insoluble polymeric material or combination of polymeric materials. For example and without limitation, in one aspect, the matrix can include an ethylene vinyl acetate (EVA) copolymer, ethyl cellulose (EC), polyethylene, polyethyl acrylate, and copolymers of ethylene and ethyl acrylate and any combination thereof. In one aspect, the matrix can include an ethylene vinyl acetate co-polymer having a relative percentage of vinyl acetate in the range of from 0% to approximately 60%, including additional vinyl acetate percentages as approximately 0%, 1%, 5%, 10%, 15%, 20%, 25%, 30%, 35%, 40%, 45%, 50%, 55% and 60% and any range of percentages derived from these values. In still another aspect, the ethylene vinyl acetate co-polymer includes approximately 40% vinyl acetate.

As summarized above, the permeant composition includes at least one hydrophilic permeant, wherein the hydrophilic permeant can include at least one bioactive agent, and at least one permeability enhancer such as, but not limited to, a pH control agent. In some embodiments, the hydrophilic permeant can concurrently (with its role as permeant) or separately function as a permeability enhancer.

In addition, the permeant composition can optionally include one or more additives suitable for administration. For example, the permeant can optionally further comprise a solubility control agent, a filler (which may be referred to as a biocompatible filler in some cases), or any other conventionally known substance suitable for providing or enhancing a desired transdermal delivery of a permeant. Examples of solubility control agents and of fillers will be described later. In one aspect, the hydrophilic permeant can account for approximately about 1 weight % to approximately about 99 weight % of the patch, including additional amounts as about 5 weight %, about 10 weight %, about 15 weight %, about 20 weight %, about 25 weight %, about 30 weight %, about 35 weight %, about 40 weight %, about 45 weight %, about 50 weight %, about 55 weight %, about 60 weight %, about 65 weight %, about 70 weight %, and about 75 weight % of the patch, and including any range of weight percentages derived from these values.

As used herein, a "bioactive agent" includes any drug, chemical, or biological material that induces a desired biological or pharmacological effect. The effect can be local, such as providing for a local anesthetic effect, or it can be systemic. Such substances include broad classes of compounds normally delivered into the body, including through body surfaces and membranes, including skin. To this end, in one aspect, the bioactive agent can be a small molecule agent. In another aspect, the bioactive agent can be a macromolecular agent. In general, and without limitation, exemplary bioactive agents include, but are not limited to, anti-infectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiangiogenic drugs; antiparkinsonism drugs; antipruritics; antipsychotics; antipyretics; antispasmodics; anticholinergics; sympathomimetics; xanthine derivatives; cardiovascular preparations including potassium and calcium channel blockers, beta-blockers, alphablockers, and antiarrhythmics; antihypertensives; diuretics and antidiuretics; vasodilators including general coronary, peripheral, and cerebral; central nervous system stimulants; vasoconstrictors; cough and cold preparations, including decongestants; hormones such as estradiol and other steroids, including corticosteroids; hypnotics; immunosuppressives; muscle relaxants; parasympatholytics; psychostimulants; sedatives; tranquilizers; anti-fibromyalgia drugs; anti-psoriasis drugs; bone resorption inhibitors; agents that build bone strength; agents that reduce bone fragility; anti-incontinence drugs; anti-infertility drugs; anti-acromegally drugs; anti-edema drugs; anti-obesity drugs; bone reorption inhibitors;

anesthetics; anti-anxiety drugs; sedatives; muscle relaxants; acetylcholinesterase inhibitors; ACE inhibitors; anti-coagulants; narcotics; anti-obsessional; anti-bulimic; anti-emetic; anxiolytics; NSAIDs; antirheumatics; hypothyroidism drug treatments; NMDA receptor antagonists; NMDA receptor agonists; partial NMDA receptor agonists; ADHD treatments, anti-spasmodic drugs, anti-convulsant drugs, migraine prophlaxis drugs; benign prostatic hypertrophy drugs; sedatives; opiates; pulmonary arterial hypertension drugs; hypnotics; osteoporosis drugs; anti-inflammatory drugs; diabetic glycemic control drugs; multiple sclerosis drugs; thrombocytopenia drugs; and myeloid reconstitution drugs. According to aspects of the present invention, the bioactive agent can include one or more peptides, polypeptides, proteins, nucleic acids, or other macromolecules known to be difficult to deliver transdermally with existing conventional techniques because of their size and charge. Examples of macromolecules which may be delivered in accordance with the present invention include, without limitation, oligonucleotides, siRNA, RNAi, antisense molecules, triple helix molecules, CpG oligomers, enhancer decoys, antibodies, LHRH, LHRH analogs (such as goserelin, leuprolide, buserelin, triptorelin, gonadorelin, napharelin and leuprolide), GHRH, GHRF, insulin, insulinotropin, calcitonin, octreotide, endorphin, TRH, NT-36 (chemical name: N-[[(s)-4-oxo-2-azetidinyl]-carbonyl]-L-histidyl-L-prolinamide), liprecin, pituitary hormones (eg, HGH, HMG, HCG, desmopressin acetate, etc), follicle luteoids, alpha-ANF, growth factor such as releasing factor (GFRF), beta-MSH, GH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hirudin and hirudin analogs such as hirulog, hyaluronidase, interleukin-2, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, bradykinin antagonists, CD4, ceredase, CSI's, enkephalins, FAB fragments, IgE peptide suppressors, IGFI, neurotrophic factors, colony stimulating factors, parathyroid hormone and agonists, parathyroid hormone antagonists, prostaglandin antagonists, cytokines, lymphokines, pentigetide, protein C, protein S, renin inhibitors, thymosin alpha-I, thrombolytics, TNF, GCSF, EPO, PTH, heparin, low molecular weight heparin, enoxaparin (Lovenox or Clexane), synthetic heparin, vaccines, vasopressin antagonist analogs, interferon-alpha,-beta, and -gamma, alpha-I antitrypsin (recombinant), and TGF-beta. genes; peptides; polypeptides; proteins; oligonucleotides; nucleic acids; and polysaccharides, glucagon-like peptide-1 analogues, and Amy Hn analogues.

As used herein, the term "peptide" refers to peptides of any length and includes proteins. The terms "polypeptide" and "oligopeptide" are used herein without any particular intended size limitation, unless a particular size is otherwise stated. Exemplary peptides that can be utilized include, without limitation, oxytocin, vasopressin, adrenocorticotrophic hormone, epidermal growth factor, prolactin, luliberin or luteinising hormone releasing hormone, growth hormone, growth hormone releasing factor, insulin, somatostatin, glucagon, interferon, gastrin, tetragastrin, pentagastrin, urogastroine, secretin, calcitonin, enkephalins, endorphins, angiotensins, renin, bradykinin, bacitracins, polymixins, colistins, tyrocidin, gramicidines, and synthetic analogues, modifications and pharmacologically active fragments thereof, monoclonal antibodies and soluble vaccines. It is contemplated that the only limitation to the peptide or protein drug which may be utilized is one of functionality.

Examples of peptide and protein drugs that contain one or more amino groups include, without limitation, anti-cancer agents, anti-angiogenic agents, pro-angiogenic agents, antibiotics, anti-emetic agents, antiviral agents, anti-inflammatory and analgesic agents, anesthetic agents, anti-ulceratives, agents for treating hypertension, agents for treating hypercalcemia, agents for treating hyperlipidemia, etc., each of which has at least one primary, secondary or tertiary amine group in the molecule, preferably, peptides, proteins or enzymes such as insulin, calcitonin, growth hormone, granulocyte colony-stimulating factor (G-CSF), erythropoietin (EPO), bone morphogenic protein (BMP), interferon, interleukin, platelet derived growth factor (PDGF), vascular endothelial growth factor (VEGF), fibroblast growth factor (FGF), nerve growth factor (NGF), urokinase, etc. can be mentioned. Further examples of protein drugs include, without limitation, insulin, alpha-, beta-, and gamma-interferon, human growth hormone, alpha- and beta-I-transforming growth factor, granulocyte colony stimulating factor (G-CSF), granulocyte macrophage colony stimulating factor (G-MCSF), parathyroid hormone (PTH), PTH analogs (Teriparatide, Ostabolin-C) human or salmon calcitonin, glucagon, somatostatin, vasoactive intestinal peptide (VIP) and its active N-terminal fragments, LHRH analogs, endostatin, angiostatin, thrombospondin, Anakinra (IL-IRA) (Kineret), Alefacept (Amevive), Aldesleukin (Proleukin), Calcitonin (Miacalcin), Corticotropin (adrenocorticotropic hormone/Acthar), Efalizumab (Raptiva), Epoetin Alfa (Epogen), Etanercept (Enbrel), Exendin-4 or Exenatide (Byetta), Filgrastim (Neupogen), Follitropins (Gonal-F), Glatiramer Acetate (Copaxone), Human Growth Hormone (Somatropin, Norditropin, Genotropin, Nutropin), Interferon Beta Ia (Avonex, Rebif), Interferon Beta Ib (Betaseron), Menotropins (Pergonal, Repronex), Octreotide (Sandostatin), Oprelvekin (Neumega), Sagramostim (Leukine), Teriparatide (Forteo), Thyrotropin Alpha (Thyrogen), insulin, inhaled insulin (Exubera), Insulin aspart (Novolog), Insulin glulisine (Apidra), Insulin lispro (Humalog), Isophane Insulin, Insulin detemir (Levemir), Insulin glargine (Lantus), Insulin zinc extended (Lente, Ultralente), Pramlintide acetate (Symlin), Growth hormone, somatotropin (Genotropin, Humatrope, Norditropin, NorlVitropin, Nutropin, Omnitrope, Protropin, Siazen, Serostim, Valtropin), Mecasermin (Increlex), Mecasermin rinfabate (IPlex), Factor VIII (Bioclate, Helixate, Kogenate, Recombinate, ReFacto), Factor IX (Benefix), Antithrombin III (Thrombate III), Protein C concentrate (Ceprotin), beta-Gluco-cerebrosidase (Cerezyme, Ceredase), Alglucosidase-alpha (Myozyme), Laronidase (Aldurazyme), Idursulphase (Elaprase), Galsulphase (Naglazyme), Agalsidase-beta (Fabrazyme), alpha-1-Proteinase inhibitor (Aralast, Prolastin), Lactase (Lactaid), pancreatic enzymes (lipase, amylase, protease) (Arco-Lase, Cotazym, Creon, Donnazyme, Pancrease, Viokase, Zymase), Adenosine deaminase (Adagen), Pooled immunoglobulins (Octagam), Human albumin (Albumarc, Albumin, Albuminar, AlbuRx, Albutein, Flexbumin, Buminate, Plasbumin), Erythropoietin, Epoetin-alpha (Epogen, Procrit), Darbepoetin-alpha (Aranesp), Filgrastim (granulocyte colony stimulating factor; G-CS F) (Neupogen), Peg-filgrastim (Peg-G-CS F) (Neulasta), Sargramostim (granulocyte-macrophage colony stimulating factor; GM-CS F) (Leukine), Oprelvekin (interleukinl 1; IL-I 1) (Neumega), Human follicle-stimulating hormone (FSH) (Gonal-F, Follistim), Human chorionic gonadotropin (HCG) (Ovidrel), Lutropin-alpha (Luveris), Type I alpha-interferon, interferon alfacon 1 (Infergen), Interferon-alpha-2a (Roferon-A), PegInterferon-alpha-2a (Pegasys), Interferon-alpha-2b (Intron A), PegInterferon-alpha-2b (Peg-Intron), Interferon-alpha-n3 (Alferon N), Interferon-beta-1 a (Avonex, Rebif), Interferon-beta-lb (Betaseron), Interferon-gamma-lb (Actimmune), Aldesleukin (interleukin 2 (IL2), epidermal thymocyte activating factor; ETAF) (Proleukin), Alteplase (tissue plasminogen activator; tPA) (Activase), Reteplase (deletion mutein of tPA) (Retavase), Tenecteplase (TNKase), Urokinase (Abbokinase), Factor Vila (Novo-Seven), Drotrecogin-alpha (activated protein C) (Xigris), Salmon calcitonin (Fortical, Miacalcin), Teriparatide (human parathyroid hormone residues 1-34) (Forteo), Octreotide (Sandostatin), Dibotermin-alpha (recombinant human bone morphogenic protein 2; rhBMP2) (Infuse), Recombinant human bone morphogenic protein 7 (rhBMP7) (Osteogenic protein 1), Histrelin acetate (gonadotropin releasing hormone; GnRH) (Supprelin LA, Vantas), Palifermin (keratinocyte growth factor; KGF) (Kepivance), Becaplermin (platelet-derived growth factor; PDGF) (Regranex), Trypsin (Granulex), Nesiritide (Natrecor), Botulinum toxin type A (Botox), Botulinum toxin type (Myoblock), Collagenase (Santyl), Human deoxyribonuclease I, dornase-alpha (Pulmozyme), Hyaluronidase (bovine (Amphadase, Hydase), ovine (Vitrase)), Hyaluronidase (recombinant human) (Hylenex), Papain (Accuzyme, Panafil), L-Asparaginase (ELSPAR), Peg-asparaginase (Oncaspar), Rasburicase (Elitek), Lepirudin (Refludan), Bivalirudin (Angiomax), Streptokinase (Streptase), Anistreplase (anisoylated plasminogen streptokinase activator complex; APSAC) (Eminase), Bevacizumab (Avastin), Cetuximab (Erbitux), Panitumumab (Vectibix), Alemtuzumab (Campath), Rituximab (Rituxan), Trastuzumab (Herceptin), Abatacept (Orencia), Anakinra (Antril, Kineret), Adalimumab (Humira), Etanercept (Enbrel), Infliximab (Remicade), Alefacept (Amevive), Efalizumab (Raptiva), Natalizumab (Tysabri), Eculizumab (Soliris), Antithymocyte globulin (rabbit) (Thymoglobulin), Basiliximab (Simulect), Daclizumab (Zenapax), Muromonab-CD3 (Orthoclone, OKT3), Omalizumab (Xolair), Palivizumab (Synagis), Enfuvirtide (Fuzeon), Abciximab (ReoPro), Pegvisomant (Somavert), Crotalidae polyvalent immune Fab (ovine) (Crofab), Digoxin immune serum Fab (ovine) (Digifab), Ranibizumab (Lucentis), Denileukin diftitox (Ontak), Ibritumomab tiuxetan (Zevalin), Gemtuzumab ozogamicin (Mylotarg), Tositumomab (Bexxar), $^{131}$I-tositumomab (Bexxar 1-131), Hepatitis B surface antigen (Engerix, Recombivax HB), HPV vaccine (Gardasil), OspA (LYMErix), Anti-Rhesus (Rh) immunoglobulin G (Rhophylac), Recombinant purified protein derivative (DPPD), Glucagon (GlucaGen), Growth hormone releasing hormone (GHRH) (Geref), Secretin (ChiRhoStim (human peptide), SecreFlo (porcine peptide)), Thyroid stimulating hormone (TSH), thyrotropin (Thyrogen), Capromab pendetide (ProstaScint), Indium-111-octreotide (OctreoScan), Satumomab pendetide (OncoScint), Arcitumomab (CEA-scan), Nofetumomab (Verluma), Apcitide (Acutect), Imciromab pentetate (Myoscint), Technetium fanolesomab (NeutroSpec), Cetrorelix acetate, oxytocin antagonists (atosiban, Barusiban), Romiplostim (NPlate), luteinizing hormone, somatostatin receptor agonists, peptidyl-prolyl isomerase inhibitor (Cyclosporin A), low molecular weight heparins (Lovenox, Tinzaparin, Dalteparin, Desirudin (Iprivasc), Fondaparinux (Arixtra), Idraparinux, biotinylated Idraparinux (SSR 126517), AVE5026, SR 123781, glycoprotein IIb/IIIa inhibitor (Eptifibatide: Integrilin, antibody abciximab, the non-peptide tirofiban), human B-type natriuretic peptide (Nesiritide: Natrecor), salmon calcitonin, arginine vasopressin receptor 2 agonists (Desmopressin), HIV fusion inhibitors (GP41 binding agonists: Enfuvirtide).

If desired, the bioactive agent can be present within the delivery reservoir as an undissolved anhydrous hydrophilic salt. To that end, as used herein, "hydrophilic salt" and similar terms include, without limitation, an ionic form of a bioactive agent, drug, or pharmaceutical agent, such as sodium, potassium, ammonium, trimethamine, or other cation salts thereof, sulfate or other anion salts thereof, acid addition salts of basic drugs, and base addition salts of acidic drugs. Illustrative examples of such salts include sodium diclofenac, sodium cromolyn, sodium acyclovir, sodium ampicillin, sodium warfarin, ketorolac tromethamine, amiloride HCl, ephedrine HCl, loxapine HCl, thiothixene HCl, trifluoperizine HCl, naltrexone HCl, naloxone HCl, nalbuphine HCl, buspirone HCl, bupriprion HCl, phenylephrine HCl, tolazoline HCl, chlorpheniramine maleate, phenylpropanolamine HCl, clonidine HCl, dextromethorphan HBr, metoprolol succinate, metoprolol tartrate, epinephrine bitartrate, ketotofin fumarate, atropine sulfate, fentanyl citrate, tramadol HCl, apomorphine sulfate, propranolol HCl, pindolol HCl, lidocaine HCl, tetracycline HCl, oxytetracycline HCl, tetracaine HCl, dibucaine HCl, terbutaline sulfate, scopolamine HBr, brompheniramine maleate and hydromorphone HCl.

In still another aspect, the bioactive agent can be a small molecule therapeutic. Illustrative examples of such small molecule therapeutics include Acitretin (Soriatane), Amitriptyline (Elavil), Alendronate Sodium, Arpiprazole (Abilify), Bethanechol HCl (Urecholine), Bromocriptine (Parlodel), Bumetanide (Bumex), Bupivacaine (Marcaine), Buprenorphine (Buprenex), Buspirone (BuSpar), Cetirizine HCl, Citalopram (Celexa), Chlorazepate (Tranxene), Clomipramine HCl, Cyclobenzaprine (Flexeril), Donepezil (Aracept), Doxazosin (Cardura), Enalapril (Vasotec), Enoxaparin (Lovenox), Escitalopram (Lexapro), Felodipine (Plendil), Fentanyl (Sublimaze, Duragesic), Fluoxetine (Prozac, Sarafem), Fosinipril, Galantamine HBr (Reminyl, Razadyne ER), Glipizide (Glucotrol), Granisetron (Kytril), Haloperidol (Haldol), Hydrocodone Bitartrate, Hydrocortisone acetate, Hydroxyzine HCl, Isradipine (DynaCirc), Ketorolac (Acular, Toradol), Leflunomide (Arava), Levothyroxine (Levoxyl, Levothroid, Synthroid), Lisinopril (Prinivil, Zestril), Lorazepan (Ativan), Loxapine (Loxitane), Meloxicam (Mobic), Memantine (Namemda), Methylphenidate (Ritalin, Concerta), Methimazole (Tapazole), Metoclopramide (Reglan), Metolazone (Mykrox, Zaroxolyn), Mirtazapine (Remeron), Montelukast, Nalbuphine (Nubain), Neostigmine (Prostigmin), Nortriptylene HCl, Olanzapine (Zyprexa), Ondansetron (Zofran), Oxybutynin Chloride (Ditropan XL), Oxycodone HCl, Oxymorphone (Numorphan), Palonosetron (Aloxi), Paliperidone, Paliperidone Palmitate, Paroxetine (Paxil), Pergolide (Permax), Perphenazine (Triaflon), Phenytoin Sodium, Pramipexole (Mirapex), Prochlorperazine (Compazine), Procyclidine (Kemadrin), Promethazine HCl, Propanolol HCl, Protriptyline (Vivactil), Ramipril, Risperidone (Risperdal), Ropinirole (Requip), Rosiglitazone (Avandia), Selegiline (Eldepryl) (R-(−)-Deprenyl hydrochloride), Tamsulosin (Flomax), Temazepam (Restoril), Thiethylperazine (Torecan), Tiagabine (Gabitril), Timolol, Tramadol, Treprostinil sodium (Remodulin), Tropisetron (Novaban), Wafarin sodium, ATI 5923, Zolpidem tartrate, and DPP-4 iinhibitors (sitagliptin (Januvia), vildagliptin (Galvus), Saxagliptin (BMS477118), Alogliptin (SYR-322), denagliptin (Redona), PHX1 149, TA-6666, GRC 8200/EMD 675992, MP513, PSN9301, R1579, BI 1356, PF-734200, ALS 2-0426, TS-021, AMG221, ABT-279, SK-0403, KRP-104, SSR162369, ARI2243, S 40010, PT-630, SYR-619, E3024, A-899301).

In still another aspect, the bioactive agent can be a therapeutic agent conventionally known for injection administration. Illustrative examples of such therapeutic agents include adenosine, Fluorouracil, Alprostadil, Amikacin Sulfate, Amiodarone, Azithromycin, Bleomycin, Carboplatin, Ceftriaxone, Ciprofloxacin, Cisplatin, Dacarbazine, Daunorubicin HCl, Deferoxamine Mesylate, Desmopressin Acetate, Dexamethasone Sodium Phosphate, Dipyridamole, Doxorubicin HCl, Enalaprilat, Epirubicin HCl, Fluconazole, Fludarabine Phosphate, Flumazenil, Fosphenytoin Sodium, Granisetron HCl, Haloperidol Decanoate, Haloperidol, Idarubicin HCl, Ifosfamide, Irinotecan HCl, L-Cysteine HCl, Leucovorin Calcium, Leuprolide Acetate, Medroxyprogesterone Acetate, Mesna, Methylprednisolone Acetate, Metoclopramide, Mitoxantrone, Norepinephrine Bitartrate, Octreotide Acetate, Ondansetron, ONXOL® (paclitaxel), Oxytocin, Pamidronate Disodium, Pancuronium Bromide, Promethazine HCl, Propofol, Sulfamethoxazole and Trimethoprim, Terbutaline Sulfate, Testosterone Cypionate, Tobramycin, TOPOSAR® (Etoposide), Vecuronium Bromide, VINCASAR PFS® (Vincristine Sulfate), Vinorelbine Tartrate, ZANOSAR® (Streptozocin), Abraxane, Acthrel, Adensocan, Alimta, Amevive, Amikacin, Anzemet, Arimidex, Arixtra, Aromasin, Avastin, Avonex, Betaseron, BICNU, Botox, Campath, Camptosar, Casodex, CeeNu, Cerezyme, Cetrotide, Copaxone, Copegus, Cytoxan, DepoTestosterone, Dobutamine, Doxil, Eligard, Eloxatin, Elspar, Enbrel, Erbitux, Ethyol, Fabrazyme, Faslodex, Follistim, Fuzeon, Ganirelex (Antagon), Gemzar, Genotropin, Genotropin Minquick, Gleevec, Gonal-F, Herceptin, Hexalen, Humatrope, Humira, Hycamtin, Infergen, Infumorph, Intron A, Kineret, Kuvan, Lior Intra, Lucentis, Lupron Pediatric, Macugen, Matulane, Menopur, Mustargen, Myobloc, Nabi-HB, Neumega, Neupogen, Nexavar, Norditropin, Nutropin, Nutropin AQ, Orencia, Ovidrel, Pegasys, Peg-Intron, Pentam, Prograf, Proleukin, Pulmozyme, Rebetol, Rebif, Reclast, Refludan, Remicade, Repronex, Revlimid, Ribapak, Ribavirin, Risperdal Consta, Rituxan, Roferon-A, Saizen, Sandostatin LAR, Serostim, Sprycel, Supprelin LA, Sutent, Synagis, Synthroid, Tarceva, Tasigna, Tamoxifen, Taxotere, Temodar, Tevtropin, Thalomid, Thyrogen, Tobi, Tubersol, Tysabri, Tykerb, Velcade, Vesanoid, Vidaza, Vinblastine, Vincristine, Viread, Vistide, Vitamin K, Vivitrol, Xeloda, Zometa, Advate, Alphanate, Alphanine, Aranesp, Bebulin, Benefix, Epogen, Forteo, Fragmin, Helixate, Hemofil, Humate, Hyate, Koate, Kogenate, Leukine, Lovenox, Monoclate, Mononine, Myochrysine, Neulasta, Neumega, Novarel, Novoseven, Procrit, Profilnine, Raptiva, Rebetron, Recombinate, Refacto, Caverject, D. H. E. 45, Zofran, Bayrho D, Protropin, Delatestryl, Plenaxis, Hemofil-M, Monarc-M, Proplex T, Hyalgan, Supartz, Synvisc, Ellence, Zoladex, Pergonal, Carimmune, Gamimune N, Gammagard, Gammar, Iveegam, Panglobulin, Polygam, and Venoglobulin. The bioactive agent portion of the permeant composition can account for from approximately 1 weight % to approximately 99 weight % of the total patch weight, including additional amounts of about 5 weight %, about 10 weight %, about 15 weight %, about 20 weight %, about 25 weight %, about 30 weight %, about 35 weight %, about 40 weight %, about 45 weight %, about 50 weight %, about 55 weight %, about 60 weight %, about 65 weight %, about 70 weight %, and about 75 weight % of the patch. Additionally, the bioactive agent can account for an amount in any range of weight percentages derived from these values, including for example an amount in the range of from about 1 to about 10 weight %, about 1 to about 30 weight %, or even an amount in the range of from about 1 to about 60 weight %.

According to one aspect, the present invention is a patch which contains exenatide and at least one permeation enhancer. The permeation enhancer can be any permeation enhancer described herein. In a particular embodiment, the permeation enhancer is a pH control agent. In a specific embodiment, the pH control agent is selected from disodium citrate, succinic acid or tris. In one embodiment, the patch contains a polymer matrix, wherein the polymer may be any polymer described above with respect to the first aspect of the invention. In another embodiment, the patch contains a reservoir matrix. In yet another embodiment, the patch further comprises a solubility control agent, wherein the solubility control agent may be any solubility control agent described above with respect to the first aspect of the invention. In a still further embodiment, the exenatide is delivered to the subject for a period of administration, wherein the period of administration may be any period described above with respect to the first aspect of the invention. In a particular embodiment, the exenatide is delivered to a subject for a period of administration selected from about 24 hours, about 3 days or about 7 days.

In one embodiment, the permeant composition disposed in the matrix can include a means for selectively controlling the pH of the biological environment in which at least one formed pathway through the biological membrane exists, for selectively controlling the pH of biological moisture received by the matrix, or a combination thereof. As noted above, the means for controlling pH can be a pH control agent disposed in the matrix. The pH control agent can be adapted to dissolve in biological moisture received from the subject when the surface of the matrix is positioned in fluid communication with at least one formed pathway through the biological membrane of the subject. The pH control agent is provided in the matrix to adjust at least a portion of contacted biological moisture to a non-physiological pH and to maintain the solubility of the hydrophilic permeant, which may be, for example, the bioactive agent. Further, according to some aspects, the pH control agent is also capable of maintaining the contacted biological moisture at a non-physiological pH for a permeant administration period of at least about 12 hours, at least about 18 hours, at least about 24 hours, at least about 3 days, or even at least about 7 days. In other aspects, a permeability enhancer may work in as little as about 1, about 3, about 5, about 7, about 10, about 15, about 20, or about 30 minutes thereby increasing the flux for several hours via a mechanism unrelated to pH. In other embodiments, bioactive agent loading in a matrix, alone, is sufficient to maintain pore permeability of formed pathways in a biological membrane for extended administration periods up to and even exceeding 12 hours, 18 hours, 24 hours, at least 3 days, and even at least 7 days. However, this is not always true in all cases or with all bioactive agents. It has now been determined according to the methods and devices of the present invention that the pH levels of the biological environment in which the formed pathway is contained can be adjusted away from physiological pH levels in order to enhance or extend the permeability of the formed pathway. Without intending to be limited by theory, it is believed that maintaining the pH or other aspects of the biological environment at levels other than physiological may delay processes that are triggered in response to perturbation of the biological membrane. Another possibility is that chelation plays a role in the effectiveness of these pH control agents. It is to be noted that although pH control agents are all able to control pH, pH control itself may not necessarily be the mechanism by which permeability enhancement occurs. Furthermore, it is to be understood that pH control agents are only one type of permeability enhancer, but that all permeability enhancers are to be considered part of this invention.

Physiological pH is conventionally known as approximately 7.4. Therefore, non-physiological pH as used herein refers to any pH value other than 7.4, including pH values less than or equal to 7.3 or pH values greater than or equal to 7.5. To that end, it should be understood that the desired level of pH to be achieved by the presence of the pH control agent will depend, at least in part, upon the particular bioactive agent to be delivered. In some aspect, the pH control agent can be select to obtain an acidic non-physiological pH level. For example, an acidic non-physiological pH can be in the range of from 2 to 6, including pH levels of about 3, 3.5, 4, 4.5, 5, 5.5 and any range of pH levels derived from these values. Alternatively, in other aspects, the pH control agent can be selected to obtain a basic or alkaline non-physiological pH level. For example, a basic non-physiological pH can be in the range of from 8 to 10, including pH levels of about 8.5, 9, or 9.5.

Exemplary and non-limiting examples of suitable pH control agents include tris(riydroxymetriyl)aminometriane (TRIS), TRICINE, 4-(2-hy droxyethy I)-I-piperazineethanesulfonic acid (HEPES), N,N-Bis(2-hydroxyethyl)-2-aminoethanesulfonic acid (BES), 2-(N-morpholino) ethanesulfonic acid (MES), imidazole, 2-amino-2-methyl-1,3-propanediol (AMPD), amino acids such as Lysine, Arginine, Histidine, Aspartic acid, Glutamic acid, and Glycine; aminosugars such as glucosamine and galactosamine; uronic and aldonic acids such as glucuronic and gluconic acid; monocarboxylic acids such as glycolic or lactic acid, dicarboxylic acids such as tartaric, malonic, maleic, fumaric, malic, succinic acid and their monosodium salts or tricarboxylic acids such as citric acid and its mono, di, and trisodium salts; inorganic salts with buffering properties such as monosodium phosphate, monopotassium phosphate, disodium phosphate, dipotassium phosphate, trisodium phosphate, sodium bicarbonate, and sodium carbonate.

The pH control agent can be present in any amount capable of achieving a desired level of pH control as described above. For example, the pH control agent portion of the permeant composition can account for from approximately 1 weight % to approximately 99 weight % of the total patch weight, including additional amounts of about 5 weight %, about 10 weight %, about 15 weight %, about 20 weight %, about 25 weight %, about 30 weight %, about 35 weight %, about 40 weight %, about 45 weight %, about 50 weight %, about 55 weight %, about 60 weight %, about 65 weight %, about 70 weight %, and about 75 weight % of the patch. Additionally, the pH control agent can account for an amount in any range of weight percentages derived from these values, including for example an amount in the range of from about 1 to about 10 weight %, about 1 to about 30 weight %, about 30 to about 60 weight %, or even an amount in the range of from about 1 to about 60 weight %.

According to one aspect, the present invention is a patch which contains at least one permeant and at least one pH control agent selected from succinic acid or tris. The permeant may be any permeant described herein. In a specific embodiment, the permeant is selected from insulin, hydromorphone, exenatide or fentanyl citrate. In another embodiment, the patch contains a polymer matrix, wherein the polymer may be any polymer described above with respect to the first aspect of the invention. In a still further embodiment, the patch contains a permeant reservoir. In a still further embodiment, the permeant is delivered to the subject for a period of administration, wherein the period of administration may be any period described above with respect to the first aspect of the invention. In a particular embodiment, the permeant is delivered to a subject for a period of administration selected from about 24 hours, about 3 days or about 7 days.

In one embodiment, the permeant composition includes an additive wherein said additive can comprise a solubility control agent, a filler, or both. The additive can include a means for selectively controlling the rate at which a bioactive agent contained within a matrix is released from the matrix. The means for controlling the release rate of bioactive agent from the matrix can be a solubility control agent capable of controlling the dissolution of a bioactive agent in biological moisture received by the matrix. In some aspects, an exemplary solubility control agent can include agents that selectively control pH of a solution relative to the isoelectric point of a particular bioactive agent. Maintaining the pH of a solution at or relatively near the isoelectric point of a bioactive agent can be used to minimize the solubility of a particular bioactive agent in the medium, such as biological moisture. According to principles of equilibrium, as portions of dissolved bioactive agent are delivered to a subject via at least one formed pathway through the biological membrane additional undissolved portions of bioactive agent remaining in the matrix can then dissolve into the received biological moisture. Thus, by optimizing the desired pH of a solution relative to the isoelectric point of a bioactive agent, the rate of dissolution of the bioactive agent can be selectively controlled. In this manner, by controlling the rate at which portions of the bioactive agent are dissolved in the biological moisture, a bolus or burst delivery of bioactive agent can be prevented and extended delivery profiles can be achieved. To that end, it should be understood that according to some aspects of the invention, a pH control agent as previously described herein can also function as a means for selectively controlling the rate at which a bioactive agent contained within a matrix is released from the matrix by controlling the rate at which at least a portion of the bioactive agent is dissolved or suspended in biological moisture received by the matrix. In an alternate embodiment, a solubility control agent may be used to maintain high solubility of the bioactive agent. In some embodiments, in order to maintain sustained drug delivery throughout the patch application period, release from the patch must be controlled using a polymer or combination of polymers.

In alternative aspects, the solubility control agent can be an ionic strength control agent, which selectively controls the ionic strength of a solution. As one of ordinary skill in the art will appreciate, the solubility of a particular bioactive agent in a medium such as biological moisture can depend at least in part upon the ionic strength of the medium itself. To that end, by increasing the ionic strength of the biological moisture received by the matrix, the solubility of a particular bioactive agent can be reduced to inhibit the bolus or burst delivery of the bioactive agent. According to principles of equilibrium, as portions of dissolved bioactive agent are delivered to a subject via the at least one formed pathway through the biological membrane additional undissolved portions of bioactive agent remaining in the matrix can then dissolve into the received biological moisture. In this manner, by controlling the rate at which portions of the bioactive agent are dissolved in the biological moisture, extended delivery profiles can be achieved.

Ionic strength controlling agents by this definition could include salts of ionic compounds comprising of anions and cations so that the product is electrically neutral. Salt forming cations include but not limited to are as follows; sodium, potassium, magnesium, iron, calcium, ammonium or pyridinium. Anions of salts included but not limited to are as follows; acetate, carbonate, chloride, citrate, nitrate, hydroxide, phosphate or sulfate. The resultant ionic salts from combination of an anion and cation could include but not limited to are sodium citrates (mono, do or tri valent salts), potassium phosphates, sodium sulfates, ammonium phosphate or sulfates, sodium chloride, etc.

In still further aspects, a solubility control agent can be a salting-out agent. As used herein, a salting-out agent can include any biocompatible material, compound, or preferably a multivalent (highly water soluble) salt that can generate a solution of a high ionic strength corresponding to a salt concentration IM or higher. For example and without limitation, in one aspect the salting-out agent can comprise ammonium, sodium or potassium sulfate, disodium or dipotassium phosphate, trisodium phosphate, di or trisodium citrate, disodium salts of dicarboxylic acids such as sodium succinate.

Salting-out agents as described in the embodiment control the dissolution rate of the bioactive agent inside the matrix. Agents such as buffers and plasticizers could enhance or retard aqueous solubility of an active agent. It has been discovered that some agents, when used in water insoluble polymer matrices, can control the dissolution rate of the bioactive agent due to its solubility effect. Agents which retard the aqueous solubility of an active agent will slow down the dissolution rate of the active agent into the dissolution media.

It is to be understood that certain water soluble polymers can function as solubility control agents. The optional solubility control agent can be present in any amount capable of achieving a desired rate of dissolution of a bioactive agent in the biological moisture received by the matrix. For example, when present, the solubility control agent portion of the permeant composition can account for from approximately 1 weight % to approximately 99 weight % of the total patch weight, including additional amounts about 5 weight %, about 10 weight %, about 15 weight %, about 20 weight %, about 25 weight %, about 30 weight %, about 35 weight %, about 40 weight %, about 45 weight %, about 50 weight %, about 55 weight %, about 60 weight %, about 65 weight %, about 70 weight %, and about 75 weight % of the patch. Additionally, the solubility control agent can account for an amount in any range of weight percentages derived from these values, including for example an amount in the range of from about 1 to about 10 weight %, about 1 to about 30 weight %, about 30 to about 60 weight %, or even an amount in the range of from about 1 to about 60 weight %.

As noted above, by controlling the rate of dissolution of bioactive agent into the biological moisture received by or absorbed into the matrix, the burst or bolus delivery of the bioactive agent can be prevented, if this is so desired. To that end, according to aspects of the invention, extended delivery profiles can be accomplished by ensuring a therapeutic amount of bioactive agent remains in the matrix after specified administration periods in which the matrix has been in fluid communication with the at least one formed pathway of a biological membrane. For example, according to some aspects, a therapeutic amount of undissolved bioactive agent can remain disposed in the matrix after the surface of the matrix is positioned in fluid communication with the at least one formed pathway for an administration period of at least 12 hours; at least 18 hours, at least 24 hours, at least 36 hours or even 7 days. As noted above, this remaining therapeutic amount can eventually dissolve into biological moisture pursuant to the presence of the solubility control agent. However, by virtue of a therapeutic amount remaining in the matrix beyond extended periods of time, the bolus or burst delivery can be prevented, affording the ability to achieve desired flux of the bioactive agent for extended periods of time.

It is to be noted that the present invention can also be used to improve delivery when a bolus delivery profile is desired. In one embodiment, bioactive agents like enoxaparin and other low molecular weight heparin compounds are delivered more effectively as a bolus by use of the invention described herein. Here, administration times may be about 5, 4, 3, 2, 1 minute or less than 1 minute. In alternate embodiments, administration times may be greater than 5 minutes and even greater that 12 hours.

In addition to the optional solubility control agent, the permeant composition can also include one or more fillers. Exemplary fillers can include any one or more of an excipient, hygroscopic agent, osmotic agent, anti-healing agent, anti-clotting agent, anti-inflammatory, anti-microbial agents, anti-irritant, reepitheliating inhibitory agent, nitrous oxide production inhibitory agent, melanogenesis inhibitory agents, dosing agent, emollient, plasticizer, humectant, chelators, and the like. The hydrophilic permeant itself can also exhibit the functionality of one or more fillers described above. One filler can also exhibit the functionality of more than one filler described above. For example, and without limitation, an excipient can also function as an antiinflammatory agent and/or even a hygroscopic agent. The one or more fillers, when present, can account for approximately 1 weight % to approximately 99 weight % of the patch, including additional amounts as about 5 weight %, about 10 weight %, about 15 weight %, about 20 weight %, about 25 weight %, about 30 weight %, about 35 weight %, about 40 weight %, about 45 weight %, about 50 weight %, about 55 weight %, about 60 weight %, and about 65 weight % of the patch, and further including any range of weight percentages derived from these values.

As used herein, an anti-healing agent can include, for example, anti-coagulants, anti-inflammatory agents, agents that inhibit cellular migration, re-epitheliation inhibiting agents, osmotic agents, and salting-out agents. Suitable anticoagulants can comprise, for example, heparin, low molecular weight heparin, synthetic heparin, pentosan polysulfate, citric acid, citrate salts, EDTA, and dextrans having a molecular weight from 2000 to 10,000 daltons. Suitable anti-inflammatory agents can comprise, for example, hydrocortisone sodium phosphate, betamethasone sodium phosphate, and triamcinolone sodium phosphate. Suitable agents that inhibit cellular migration can comprise, for example, laminin and/or its related peptides. As used herein, an osmotic agent can include any biocompatible material, compound, or composition that can generate, in solution, an osmotic pressure greater than about 2000 kilopascals, or mixtures thereof. For example and without limitation, in one aspect the osmotic agent can include a biologically compatible salt such as sodium chloride or a neutral compound such as glucose, or a zwitterionic compound such as glycine having a sufficiently high concentration to generate, in solution, a desired osmotic pressure. For example, in one aspect, an osmotic agent, in solution, can generate an osmotic pressure greater than about 2000 kilopascals. In another aspect, an osmotic agent can generate an osmotic pressure greater than about 3000 kilopascals.

To this end, it should be understood that in an alternative aspect, the bioactive agent can also provide the functionality of any one or more fillers described above. For example, and without limitation, a bioactive agent can also exhibit anti-healing effects as set forth above. In particular, in one aspect, the bioactive agent can generate, in solution or suspension, an osmotic pressure greater than approximately 2000 kilopascals such that it is capable of inhibiting the healing process of the at least one formed pathway through the skin of a subject.

As used herein, a hygroscopic agent is intended to include a bio-compatible material, compound or composition having an affinity for subcutaneous fluid such that when present in the permeant, it can enhance the drawing of subcutaneous fluid from the subject into the delivery reservoir. For example, and without limitation, in one aspect a suitable hygroscopic agent that can be used according to the present invention is mannitol. The addition of a hygroscopic filler material may also serve as an attractant to fluid exuding from the treated skin, helping to bring the fluid into the reservoir and in contact with the bioactive agent, while also working to create more diffusion channels from the skin surface side of the reservoir into the body of the reservoir where more bioactive agent can be accessed. Such filler materials should be selected so as to minimize any inhibition of the bioactive agent being delivered into the subject once solubilized and/or suspended.

In one aspect, the filler can include glycerin, propylene glycol (PG), or a combination thereof. When incorporated as at least a portion of the filler, glycerin and/or propylene glycol can function as one or more of a humectant, hygroscopic agent, emollient, plasticizer, antimicrobial, skin permeation enhancer, and/or anti-irritant. Still further, it should be understood that glycerin and propylene glycol can also be effective for use in increasing the release rate of a bioactive agent from a matrix as described herein and increasing bioactive agent utilization. When used, glycerin and/or propylene glycol are typically present in an amount in the range of from approximately greater than 0.0% by weight to approximately 5.0 weight % of the patch, including amounts of about 0.5 weight %, about 1.0 weight %, about 1.5 weight %, about 2.0 weight %, about 2.5 weight %, about 3.0 weight %, about 3.5 weight %, about 4.0 weight %, about 4.5 weight %, and any range derived from the aforementioned weight percentages.

In another aspect, the filler can be selected such that the pH of the fluid it contacts is kept acidic. This can impart an inherent antimicrobial activity against a variety of microorganisms including, without limitation, bacteria, yeast, and mold. In addition, one or more antimicrobial agents can also be added to the polymer film formulation to further enhance the antimicrobial activity of the film.

In one embodiment, an exemplary patch or system that includes a porator and a patch according to the present invention provides a method for causing the transdermal flux of a permeant into a subject via at least one formed pathway through a skin layer of the subject. In one aspect, the method includes providing a subject having a transdermal permeant administration site comprising at least one formed pathway through a biological membrane, such as a skin layer. As described above, the subject can be any living organism having at least one biological membrane capable of having a bioactive agent delivered or administered through at least one pathway formed there through. Exemplary subjects can be a mammal, such as, for example, a human subject. In an alternative aspect, the subject can be non-mammalian. In still another aspect, the methods and systems of the present invention can be used on a plant.

It will be appreciated upon practicing the present invention that utilizing an anhydrous reservoir design including undissolved permeant composition can improve the shelf stability of the product, reducing the need for refrigeration in many cases. For example, in the case of a protein, peptide, or vaccine antigen, the ability to store the product without refrigeration is an advantage, eliminating the need for refrigeration throughout the distribution network. In the case of vaccine patches, this is an attribute which would allow distribution of vaccines throughout the world without the requirement of a reliable cold chain. The use of an anhydrous formulation can provide still other benefits, including the inherent antimicrobial activity presented by a formulation that does not contain water, and the ability to provide physically smaller reservoirs, as there is no required concentration needed to maintain a stable permeant solution. It is to be noted that the invention also provides for embodiments where an adjuvant (such as a normally non-permeant molecule as well as peptides) is co-delivered with the antigen in the same patch as means to conveniently boost the immune response. As illustrated in FIG. 1, a device according to one embodiment of the present invention includes a matrix 20 having a top surface 22 and an opposed bottom surface 24. The permeant composition as described above is further disposed within the matrix. In one embodiment, the permeant composition, including a hydrophilic permeant and a permeation enhancer like a pH control agent, can come in contact with biological moisture when the bottom surface of the matrix is positioned in fluid communication with the at least one formed pathway through the biological membrane of a subject. Once an effective amount of biological moisture has come into contact with the matrix, the moisture subsequently provides a diffusion path for delivering at least a portion of the hydrophilic permeant and, optionally, at least a portion of the permeation enhancer back through the biological membrane into the subject. For example, in one aspect and without limitation, the permeant composition can have an affinity for subcutaneous fluid such that at least a portion of the permeant composition can draw an effective amount of subcutaneous fluid from the subject when the bottom surface of the matrix is positioned in fluid communication with at least one formed pathway through the skin layer of a subject. It will be appreciated upon practicing the present invention that in one aspect an undissolved hydrophilic permeant disposed within the matrix is not transdermally active or available for transdermal delivery until first coming in contact with subcutaneous fluid drawn from the subject. Furthermore, conventional implantable or oral delivery systems using highly water-soluble drug forms typically experience a burst effect seen in the resulting PK profiles. However, by keeping the matrix of hydrophilic permeant on the skin surface, and providing a matrix, hydrophilic permeant, and a permeation enhancer like a pH control agent that can ensure a specified release rate, this burst effect can be eliminated by the permeant compositions of the instant invention. In an exemplary aspect, the matrix can be constructed and arranged such that it has a porosity that defines a plurality of interconnected conduits wherein at least a portion of the plurality of conduits are in communication with the matrix bottom surface. According to this aspect, the undissolved hydrophilic permeant, and optionally, the permeation enhancer like a pH control agent can be disposed within at least a portion of the plurality of conduits of the matrix. This exemplified matrix is thereby adapted to use biological moisture drawn through at least one formed pathway through the biological membrane to dissolve or suspend at least a portion of the permeant, and optionally, the permeation enhancer like a pH control agent disposed within the matrix, thereby enabling diffusion or transport of the dissolved agent(s) through the biological membrane and into the subject.

Various mechanisms of transport can affect the dispersion and movement of the permeant composition from the matrix into the skin tissues. In one embodiment, a permeant disposed within the matrix becomes available to the organism upon release by leaving the micro-particulate form and typically going into solution or suspension in the surrounding tissue. Once in solution or suspension, diffusion can provide the transport mechanism for the micro-particulate permeant via the treated outer layers and into or through the viable layers of the skin and into the subject. As the process continues over time, the voids formed by the permeant that leaves the patch and moves into the skin form channels penetrating into the body of the matrix thereby providing additional access to more permeant than was initially present at the surface of the matrix. Accordingly, by placing the matrix in communication with at least one formed pathway through a skin layer of a subject, subcutaneous fluid can provide an effective amount or level of hydration to the matrix to dissolve or suspend the permeant. As such, a relatively high concentration of permeant in solution or suspension can be provided that is also in communication to the viable tissue layers of the skin. Again, it is to be noted that the permeation enhancer like a pH control agent can accompany the permeant in any one, multiple, or all steps of this process and all processes described through this application. By forming a patch according to the present invention, it will be appreciated that it is possible to achieve a relatively high level of permeant utilization not heretofore realized by conventional transdermal delivery devices, systems and methods known for transdermal permeant delivery. Conventional transdermal products rarely utilize more than approximately 30-40% of the bioactive agent present within the patch. However, using a conventional residual analysis, the delivery matrices of the present invention can, in one aspect, provide a permeant utilization in the range of from approximately 10% to approximately 100%, including such permeant utilizations of about 15%, about 20%, about 25%, about 30%, about 35%, about 40%, about 45%, about 50%, about 55%, about 60%, about 65%, about 70%, about 75%, about 80%, about 85%, about 90% and about 95% and including any range of permeant utilizations derived from these values.

Additionally, it will also be appreciated upon practicing the present invention that a delivery matrix according to the present invention is capable of maintaining a relatively constant, relatively high chemical potential driving force by continually dissolving or suspending undissolved permeant disposed within the matrix, thus enabling suspended or dissolved permeant in communication with at least one formed pathway to remain at or near saturation levels for extended administration periods. By using a matrix as the permeant carrier, one can effectively 'fill' the space between a plurality of formed pathways over the area of the treated skin site, with an inert, but effectively porous matrix, keeping the required volume of fluid to a minimum. In contrast, conventional methods and devices require a relatively larger quantity of permeant to create the saturation point condition in order to yield the same osmotic driving force for the permeant to enter the skin than it does when the permeant is present in an undissolved anhydrous solid form. With a traditional pure liquid or gelled aqueous formulation, it takes a much larger quantity of bioactive agent to cover the treated skin site and yield the same saturation level driving force for the bioactive agent to enter the skin than it does when the bioactive agent is present in the solid form, without any water other than that presented by the body via the micropores. In one aspect, the functionality of the system is enabled by the aqueous channels in the skin provided by altering the outermost layers of the skin such that they become permeable during the wear period to a degree sufficient to allow subcutaneous fluid to exit the subject, dissolve or suspend the bioactive agent, and then allow the dissolved or suspended bioactive agent to migrate into the body via these same aqueous channels.

The delivery matrices of the instant invention can be manufactured by any conventionally known means for providing a solid matrix having at least one undissolved hydrophilic permeant disposed therein. For example, in one embodiment where the delivery device includes a polymer matrix, the polymer and hydrophilic permeant composition, further including any permeability enhancer (like a pH control agent), solubility control agent, and/or optional filler, can be dry-mixed together using a heated kneading mixer. If the permeant includes a plurality of components, the plurality of permeant composition components can, if desired, be premixed to ensure a homogenous permeant composition prior to the mixing of the permeant with the polymeric matrix material. Such permeant pre-blending, if desired, can be performed, for example, on a conventional rotisserie mixer.

The temperature setting of the mixing system should be high enough to allow the particular polymeric material to soften such that it can be kneaded, but not so high as to induce melting of the particular permeant components. Such conditions are of course dependent on the properties of the particular polymeric matrix material and the permeant to be disposed therein. Accordingly, one of skill in the art will be able to readily obtain such operating parameters without requiring undue experimentation. The resulting heat-kneaded mixture can then processed into individual dosage forms of the delivery device comprising, for example, film sheets cut or otherwise configured into any desired shape such as a circular, elliptical, rectangular, square, or any other desired shape.

The permeant delivery device can also be manufactured in any desired thickness, including thicknesses in the range of from approximately 0.01 mm to approximately 30 mm, including such thicknesses as about 0.05, about 0.1, about 0.5, about 1.0, about 5.0, about 10.0, about 15.0, about 20.0, and about 25.0 or even any range of thicknesses derived from these values. For example, the thickness can be in the range of from about 0.01 mm to about 10.0 mm, or even about 0.5 mm to about 1.0 mm. To this end, it will be appreciated upon practicing the present invention that the desired thickness can, for example, depend on the particular matrix components and/or the desired delivery parameters for a given permeant composition delivery device. For example, in one aspect it may be desired to provide a thicker delivery film in order to provide a longer administration period. Accordingly, such customization and optimization of the particular delivery device dimensions will be readily obtained by one of skill in the art through no more than mere routine experimentation.

In one embodiment, this processing may be accomplished by melt-pressing a quantity of the heat-kneaded admix into a substantially uniform thickness and then using a conventional die cutting method to form the final shape of the delivery device. Alternatively, the processing of the admix can be achieved by extrusion of the heated admix through a die which forms a ribbon of substantial uniform width and thickness, from which the delivery device can be cut either by chopping the ribbon into desired lengths forming, for example, rectangular dosage forms, or die cutting the final dosage form out of the ribbon. In one embodiment, using a die cutting method on the extruded ribbon, the processing machinery can further be configured to recycle the excess 'edges' of the ribbon left after the die cutting procedure, back into the input feed of the mixing/extruding machine, thus achieving a near-zero loss process for mixing the raw components and forming the final dosage form of the device. Alternatively, a cryo-milled polymeric powder could be mixed with the permeant and optional other components until a substantially uniform and homogenous distribution of the permeant and polymer is achieved. The resulting mixture can then be hot or cold press formed, or melt extruded into the final desired delivery device shape. In still another aspect, a conventional solvent casting process can be used wherein the matrix material is dissolved into an organic solvent such as, for example, methylene chloride, methyl-t-butyl ether, methyl ethyl ketone, ethyl acetate, propyl acetate, isopropyl acetate, ethanol, acetone or their binary/tertiary mixtures. The undissolved permeant and optional other components can then be added to the dissolved polymeric matrix material and the resulting suspension can then poured into forms having the desired size and shape. The solvent, such as the methylene chloride, can then be evaporated or otherwise removed to provide the permeant delivery device.

As one of skill in the art will appreciate, the relative amounts of bioactive agent(s), permeability enhancer(s) (like pH control agents), solubility control agent(s), filler component(s) and matrix material can all be adjusted to provide the desired flux rate of the permeant into a subject as well as the desired duration or effective administration period. For example, the permeant can comprise a filler component, such as a dosing agent, in an amount relative to a predetermined amount of bioactive agent, which can provide a predetermined transdermal dosage of bioactive agent. Alternatively, the permeant composition itself can be present in an amount and composition, relative to a predetermined amount of the solid matrix, which can provide a predetermined rate of transdermal permeant diffusion.

In one aspect, the concentration of undissolved permeant disposed within the anhydrous reservoir is designed to provide the desired statistical probability that upon exposure to a moisture source, such as the subcutaneous fluid obtained from the micropores in the skin, the moisture will dissolve or suspend the undissolved permeant such that aqueous channels develop into and through the matrix, progressively forming throughout the matrix until the required amount of permeant needed to be delivered to the subject through the micropores has been dissolved or suspended and diffused through these channels, through the micropores and into the subject's skin. By choosing the appropriate ratios, a matrix can be constructed which insures that substantially all of the permeant in the matrix will be accessible via these aqueous channels formed by the solution front as it moves progressively further into the matrix.

Further, optional solubility control agents and/or fillers can be included in the device to control the release rate of the bioactive agent, modify the solubility of the bioactive agent in the skin tissues, inhibit or enhance selected physiological phenomena within the affected tissue such as, but not limited to, boosting an immune response, inhibiting an inflammatory response, edema or erythema, maintaining a specified pH range in the tissue, and the like. To this end, by constructing the delivery device to provide a release rate which is more limited than the slowest rate that the skin tissues can absorb the bioactive agent, the system can be made to be extremely repeatable regardless of inter or intra subject variability that typically affect the bioactive agent delivery rate.

In one embodiment, the egress of the drug from the matrix can be controlled through the addition of a variety of polymeric species. These polymers may affect the porosity of the matrix, thereby limiting the availability of interstitial fluid to the permeant or permeability enhancer(s) and thus offering control of permeant and/or permeability enhancer (s) delivery. These polymers, especially when of the water-soluble variety, may also be able to limit the availability of interstitial fluid to the permeant and/or permeability enhancer(s) and thereby control their egress from the film. For example, interstitial fluid which is required for dissolution of the permeant or permeability enhancer(s) can be partially consumed by the dissolution of the water-soluble polymer, thus effectively controlling delivery of the other water-soluble species. Alternatively, the dissolution of a water-soluble polymer can result in an increase in viscosity of the film environment which may also act as a means to control delivery or dissolution. Alternatively, the dissolution of the polymer may result in a film environment in which the effective concentrations of the permeant or permeability enhancer(s) are lower than in the absence of dissolved polymer, thereby lowering the rate of delivery.

Figure 3:
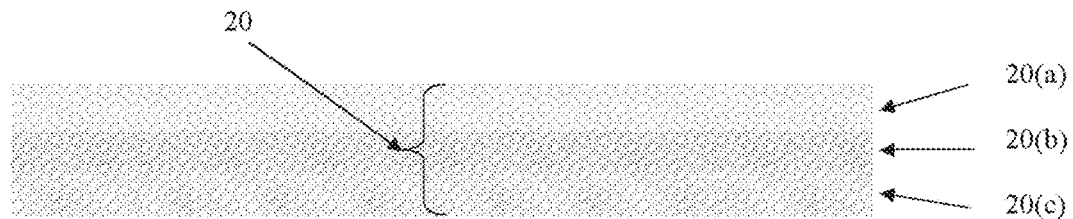
FIG. 3 illustrates a side view of a permeant delivery patch according to one aspect of the present invention where the reservoir or matrix comprises a plurality of delivery reservoirs or matrices positioned in a stacked arrangement.

It should also be understood that the device of the present invention is not limited to aspects comprising a single delivery patch, but further embodies aspects including a plurality of delivery patches. For example, as depicted in FIG. 3, in one aspect the device of the instant invention can include a plurality of delivery matrices or reservoirs positioned in a stacked arrangement. As illustrated, a delivery matrix or reservoir 20 can comprise, for example and without limitation, three permeant delivery matrices (or reservoirs), 20(*a*), 20(*b*) and 20(*c*) positioned in a stacked arrangement.

Alternatively, a device according to the present invention can include a plurality of matrices positioned in an adjacent or side-by-side relationship. In still another aspect, a device according to the present invention can include a combination of a plurality of stacked matrices and a plurality of adjacent delivery matrices. By providing a multilayered plurality of delivery matrices, wherein as each layer is sequentially accessed by the dissolution front, the predetermined release rate can be varied over a predetermined permeant administration period, thus enabling one of skill in the art to tailor the resulting PK profile of the permeant in the subject. For example, in one aspect, a plurality of delivery matrices can be provided where at least two matrices include different dimensional characteristics. In another aspect, at least two matrices can be provided, each having a different permeant composition deposited therein. In still another aspect, it is contemplated that a plurality of delivery matrices can be provided where each of the plurality of matrices includes a different permeant composition. In still another aspect, a plurality of permeant delivery matrices can be arranged to provide a predetermined pattern of pulsatile bioactive agent delivery. This can be done with a completely passive diffusion system wherein the delivery matrix is constructed with a plurality of matrix layers, some containing permeant and some not. Thus, as the solution front moves through the matrix, bioactive agent will be delivered only during those periods where the layer that contains it is at the edge of the solution front. Customizing the bioactive agent content in these multiple layers provides a transdermal delivery system which can adjust the influx to be optimal. For example, an insulin delivery system can be constructed to compliment the natural circadian cycles of a subject's glucose metabolism, thus varying the amount of bioactive agent delivered over the dosing period in a programmed fashion to provide better therapy.

Additional methods for providing permeant release rate control can include, but are not limited to, altering the physical design of the matrix, altering the tortuosity of the diffusion paths formed as the dissolution front migrates into the matrix, the choice of anhydrous polymer or other matrix material, or by the addition of specific rate-limiting mechanisms such as a specified membrane or layer within the matrix. In one embodiment, the polymer matrix can be formed with a specified texture on the skin contact surface said texture designed to increase the surface area of the skin contact surface. By increasing the surface area between the matrix and the skin, the initial rate of release of bioactive agent into the fluid interface between the patch and the micropores will be greater, resulting in a higher initial flux of the bioactive agent. As the bioactive agent within the matrix near the textured surface is depleted, and the aqueous porosities penetrating into the polymer matrix extend further into the matrix, the flux of the bioactive agent will slow down as the effect of the increased surface area becomes diminished, the further the dissolution front moves into the body of the matrix. Exemplary surface area enhancements can include, but are not limited to, corrugations, perforations, a series of holes extending into the matrix, either partially through or all the way through or a combination of partial and complete holes, with the partials all at one depth or at an assortment of depths.

Figure 2:
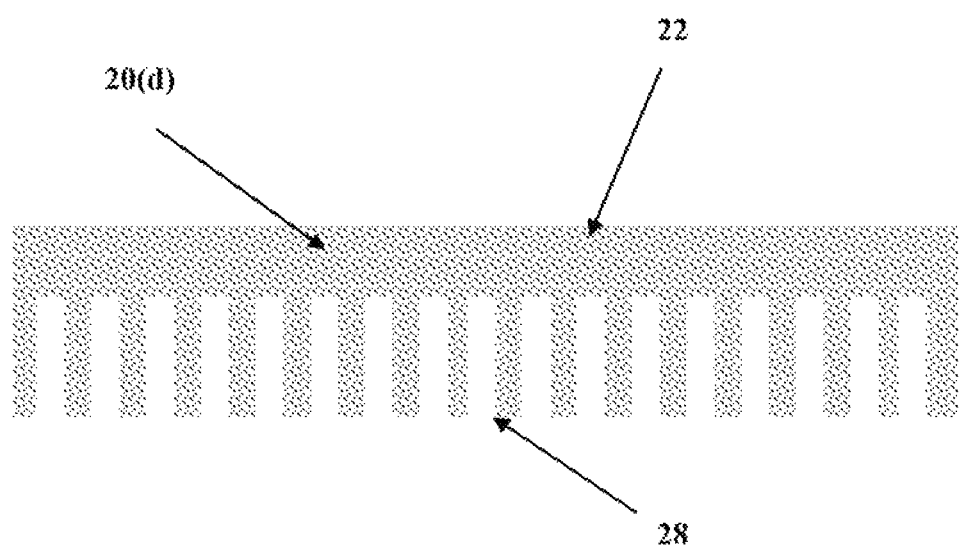
FIG. 2 illustrates a side view of a permeant delivery patch according to one aspect of the present invention where the delivery patch comprises an enhanced surface area provided by perforations.

Essentially, any physical forming of the matrix that modifies the surface area exposed to the dissolving fluid presented via the micropores, could be used to tailor the flux at various time points during the wear period. Some of the processes useful for forming the matrix in this manner include, but are not limited to, extrusion, stamping, casting, punching, die-cutting, rolling, melting, laser machining, milling, etching or hobbing process, or any combination thereof. These texturing and puncturing of the matrix in layers can be applied to internal layers that are sandwiched between other layers as well, not just to the layer placed on the surface of the skin. With reference to FIG. 2, an exemplary delivery matrix comprising an enhanced bottom surface area is depicted. As shown, a delivery matrix 20(*d*) can comprise a textured bottom surface 22 wherein the textured surface comprises a series of linear perforations 28.

It will be appreciated upon practicing the present invention that the devices described herein can be used to transdermally deliver a permeant for extended administration periods. To that end, a delivery matrix as described herein can be used to transdermally deliver a permeant to a subject over a predetermined administration period ranging from approximately 5 minutes up to approximately 400 hours or more, including administration periods of approximately 1, 5, 10, 12, 15, 18, 20, 24, 30, 36, 45, 50 minutes and approximately 1, 5, 9, 10, 12, 15, 18, 20, 24, 30, 36, 45, 50, 100, 150, 200, 250, 300 and 350 hours. Alternatively, the devices of the instant invention can be used to transdermally deliver a predetermined amount of permeant during a predetermined administration period of about 5 minutes to about 1 hour, about 1 hour to about 6 hours, about 6 to about 12 hours, about 12 to about 30 hours, about 30 to about 50 hours, about 50 to about 80 hours, about 80 to about 120 hours, and even about 120 to about 180 hours. In other embodiments, the devices of the instant invention can be used to transdermally deliver a predetermined amount of permeant during a predetermined administration period of about 1 day, about 3 days, or about 7 days.

Figure 4:
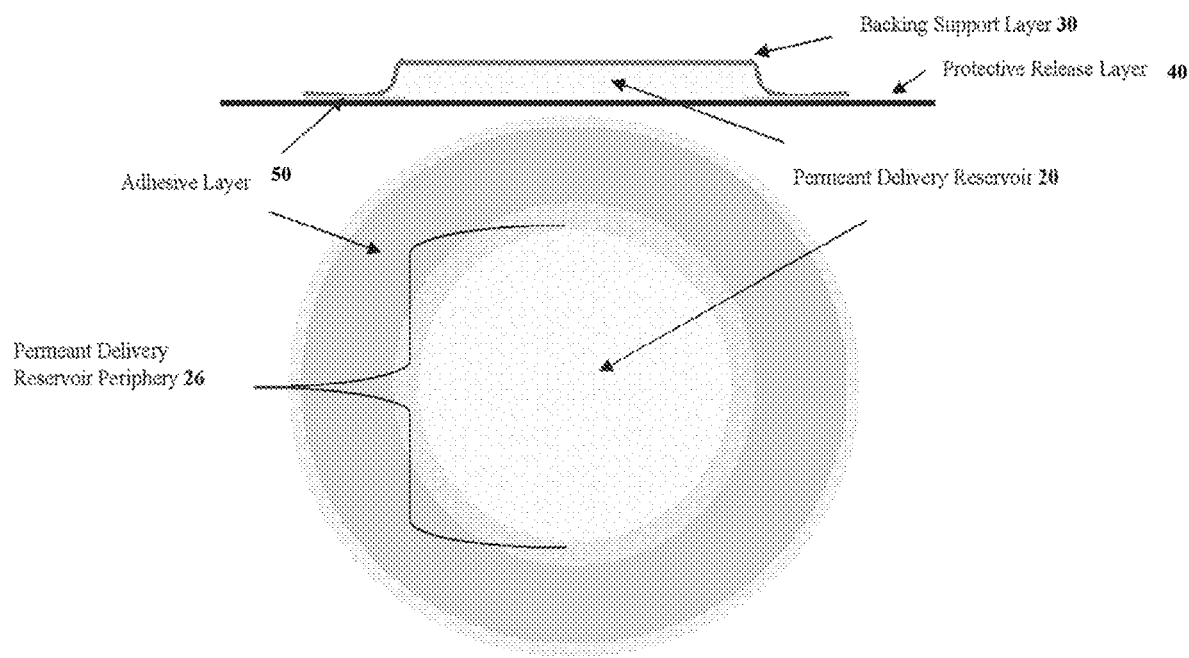
FIG. 4 illustrates an exemplary transdermal permeant delivery patch according to one aspect of the present invention.

To this end, while not intending to be limited by theory, in some aspects the relatively long administration periods achieved by the devices of the present invention can be a result of the high osmotic pressure diffusion gradient resulting from maintaining the dissolved or suspended permeant near the saturation point for extended periods of time. It is further believed that these relatively high osmotic pressure gradients can themselves provide an anti-healing influence on the formed pathway through the opening in the skin layer of a subject further enhancing the ability to achieve extended administration periods. Thus, it should be appreciated that the delivery devices of the present invention can be constructed and arranged to deliver a predetermined level of permeant over virtually any desired administration period. An exemplary device according to one aspect of the present invention is depicted in FIG. 4. As illustrated, the exemplary device provides a transdermal patch assembly, comprising a delivery matrix or reservoir 20 as previously described herein. The delivery matrix is constructed and arranged such that it has a top surface and an opposed bottom surface. A backing support layer 30, having an inwardly facing surface is at least partially connected to the top surface of the delivery matrix. In one aspect, in order to releasably affix the delivery matrix to the skin of a subject, the backing support layer can be sized and shaped such that it peripherally extends beyond the delivery matrix. Further, at least a portion of the inwardly facing surface of the peripherally extending backing support layer can further comprise an adhesive layer 50 deposited thereon. As one of skill in the art will appreciate, the adhesive layer deposited on at least a portion of the backing layer which extends beyond the periphery of the matrix can provide a peripheral adhesive attachment system.

Alternatively, it is also contemplated that the delivery matrix can be designed so as to have a skin contact surface tacky enough to releasably adhere directly to the skin of a subject. This can minimize the total size of the patch and reduce the reliance on the peripheral adhesive to maintain sufficient adhesion to adhere the patch to the skin for the duration of the patch wear period (e.g. 1, 2, 3, or 7 days). It will be appreciated upon practice of the invention disclosed herein that such a matrix can be obtained by, for example, optimizing the percentage of polymer, hydrophilic permeant, and/or permeability enhancer as well as the manufacturing process parameters. Such optimization can be determined by one of skill in the art without the need for undue experimentation.

The backing support layer 30 can in one aspect be at least substantially occlusive. Alternatively, the backing support layer can be at least partially semipermeable. To this end, in some cases, a semi-permeable backing, such as for example the 3M Tegaderm® product, can provide added user comfort as a vapor permeable backing typically having higher user tolerance for longer wear periods. In addition, the release rate of the drug into the skin can be controlled by controlling the rate of water transport through the film by designing the semi-permeable backing support layer with a specific mean vapor transmission rate (MVTR). In other cases, a more completely occlusive backing may be preferred in order to ensure the maximal hydration of the matrix from subcutaneous fluid that is accessed from at least one formed pathway beneath the patch assembly, as well as from transepidermal water loss through the intact skin surrounding and between the formed pathway(s).

Alternatively, the backing can be made totally occlusive to promote hydration of the film and thus contact with the subcutaneous fluid, while the peripheral adhesive can be made semi-permeable to allow better wear characteristics such as better adhesion, and/or lower irritation. The patch assembly can further include a peelable protective release layer 40 sized and shaped to protect at least a portion of the bottom surface of the delivery matrix from environmental elements until the device is to be used. In one aspect, the protective release layer can be removably secured to at least a portion of peripherally extending backing support layer having the adhesive layer deposited thereon. As will be appreciated, the positioning of the release layer according to this aspect not only provides protection to the bottom surface of the delivery matrix but can further add a protective layer to the adhesive layer deposited on the peripherally extending portion of the backing support layer. The patch assembly comprising the delivery matrix, backing support layer, adhesive layer and protective release layer can then placed in an individual pouch and sealed shut.

In one embodiment, an exemplary delivery matrix according to the present invention provides a method for causing the transdermal flux of a permeant into a subject via at least one formed pathway through a skin layer of the subject. In one aspect, the method comprises providing a subject having a transdermal permeant administration site comprising at least one formed pathway through the skin layer. As used herein, the subject can be any living organism having at least one skin layer capable of transdermal permeant administration. To this end, the subject can be a mammal, such as, for example, a human subject. In an alternative aspect, the subject can be non-mammalian. In still another aspect, the methods and systems of the present invention can be used on a plant.

The transdermal permeant administration site is comprised of at least one formed pathway though a skin layer of the subject. The pathway can be formed by any currently known means for providing a pathway through a skin layer of a subject. To that end, the skin treatment may be some method of forming one or more small, artificial openings, or micropores in the skin within the size range of 1-1000 microns across, including about 1 to about 500, about 100 to about 1000, about 200 to about 600, and about 400 to about 800 microns across and 1 to 500 microns deep, including about 1 to about 100, about 50 to about 100, about 70 to about 90, about 20 to about 80, about 100 to about 400, about 200 to about 300, and about 250 to about 500 microns deep which allow fluid communication between the bioactive agent or matrix and the viable cell layers of the skin beneath the outer most layers of the organism's skin, typically the stratum corneum in a human. These micropores can allow subcutaneous fluid to exude through the micropores to the surface of the skin.

In exemplary aspects, and not meant to be limiting, micropores or pathways in the skin of the subject can be formed by applying thermal poration devices, mechanically puncturing the skin with micro-needles, lancets or blades, laser ablation, radiofrequency or electrical ablation, electrical puncturing or ablation, and/or hydraulic jets. Creating pathways by mechanical methods includes use of projections such as solid microneedles or "pyramids" to puncture the skin or scrape tracks or paths through the stratum corneum. The skin treatment may also include, but is not limited to, methods such as the application of acoustic energy or sonication of the skin to increase its permeability, electroporation, tape stripping, abrasive stripping or abrasive treatments, gas jet abrasive treatments, micro-puncturing by the application of high velocity inert particles to the skin via apparatus such as those described by PowderJect Pharmaceutical PLC, chemical treatments, heat treatments, or mechanical treatments to make the skin suitably permeable. Exemplary systems, devices, and methods for forming the desired micropores are discussed in U.S. Pat. Nos. 5,885,211, 6,527,716, 6,597,794, 6,611707, 6,692,456, 6,708,060, and 6,711,435 and United States Patent Application Nos. 2004-0220456, 2004-0039342, and 2004-0039343, all of which are incorporated in their entirety herein by reference. After removal of the protective release layer, the patch assembly can then be positioned on the skin of the subject in a manner which at least substantially co-locates the bottom surface of the delivery matrix over a permeant administration site having at least one formed pathway through a skin layer of the subject, as described herein such that the permeant delivery matrix comprising an undissolved hydrophilic permeant is in fluid communication with at least one formed pathway through the skin layer of the subject. Various methods of simplifying the co-location of the active area of the patch to the microporated skin site can be incorporated into an integrated system design such as, for example, a system of visual marks left after the application of the microporation method to allow the user to place the patch in the correct position when these marks are used as reference points. These marks may be formed with markers such as, but not limited to, a dye or ink, or even simply formed by mechanical texture leaving a temporary pattern on the skin; a fold-over co-location system wherein the patch is temporarily attached to the poration system in a fashion which when the poration is accomplished and the poration system is removed from the skin site, a small 'hinge' component is left behind holding the patch such that when the patch is folded over and the hinge is flexed 180 degrees, the needed co-location is ensured; a locator ring of peripheral indicators are left on the skin after the removal of the porator system which provide the needed guides for proper placement of the patch; a fully automated applicator system is used which sequentially applies the poration system, removes it and then applies the patch in a fashion completely transparent and optionally, even hidden, to the user; a fully integrated system is used wherein the porator component is biocompatible, is directly integrated into the skin side of the patch and is designed to allow it to be left in place against the skin under the reservoir after the poration process has be accomplished. Thus, in one embodiment, the porator is porous enough to allow the required flux of fluid from the micropores to enter the matrix and the dissolved or suspended bioactive agent from the matrix, back around/across the porator and into the micropores.

In one embodiment, the permeant delivery matrix is maintained in fluid communication with the at least one formed pathway to draw an effective amount of subcutaneous fluid from the subject through the at least one formed pathway and subsequently transdermally deliver at least a portion of the permeant through the formed pathway at a desired flux. To this end, the subcutaneous fluid drawn through the at least one formed pathway can initiate the process of dissolving and/or suspending at least a portion of the permeant disposed within the matrix and subsequently can provide a viable diffusion pathway for the permeant to transdermally diffuse back into the subject through at least one formed pathway in the skin. Once the permeant has been transdermally delivered to a viable skin layer of the subject, the permeant can be active locally or can be taken up by the circulatory system and distributed systemically. For example, in one aspect, the permeant can be taken up by the lymphatic system.

In addition to the passive chemical diffusion based driving forces described herein, it is contemplated that additional permeation enhancers can also be used in combination with the permeant delivery matrices of the present invention. For example, and without limitation, the delivery matrices of the instant invention can be used in combination with an active force enhancer technology, such as the application of sonic energy, mechanical suction, pressure, or local deformation of the tissues, of which sonophoresis, iontophoresis or electroporation are included.

Still further, additional electromotive forces can also be applied to the permeant in order to enhance the transdermal permeant flux of the permeant through at least one formed pathway in the skin of the subject. The use of electromotive forces can be particularly useful for transdermal delivery of larger macromolecular agents such as proteins, peptides, and even genes in therapeutic amounts through microporated skin. Moreover, such active delivery modes can in other aspects be used with fewer and/or smaller pathways than are often needed for an equivalent flux via a passive diffusion only system. Thus, in one aspect, the use of active electromotive forces can thereby reduce the volume of skin to be ablated, making the system even less invasive for the user.

Figure 5:
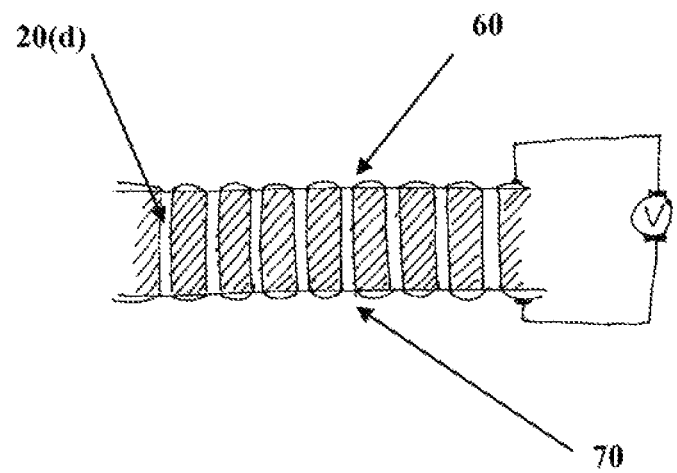
FIG. 5 illustrates a schematic diagram of an electro-osmotic pump assembly according to one aspect of the present invention.

To that end, in one aspect, a permeant delivery matrix according to the instant invention can be configured to provide an electro-osmotic-pump (EOP) assembly. According to this aspect, and as depicted in FIG. 5, a microporated delivery matrix 20(d) having a top surface and an opposed bottom surface, can further comprise an assembly of one or more first electrodes 60 positioned in electrical communication with the top surface and an assembly of one or more second electrodes 70 positioned in electrical communication with the bottom surface. The electrode assemblies can be provided by any conventional electrode deposition techniques know to one of skill in the art, such as, for example, sputtering, electro-deposition, or electro-less deposition. A complete circuit can then be created by placing the first and second electrode assemblies in selective or controllable electrical communication with a voltage or current source (V). A steady application of a properly polarized electrical field to the permeant within the microporated matrix can induce a build up of permeant in the vicinity of the openings of the microporated matrix, thus providing a relative boost to the diffusion gradient driven transdermal delivery into a subject.

In still another aspect, an electro-osmotic-pump assembly according to the present invention can further comprise a third or counter electrode remotely positioned from the delivery matrix and adapted to be positioned in electrical communication with the skin of a subject. The incorporation of a third, or counter electrode, can enable the application of an electromotive force capable of enhancing the movement of the permeant from the bottom surface of the microporated delivery matrix laterally to foci coincident with the at least one formed pathway in the skin of the subject. As will be appreciated, this aspect of the invention can provide additional transdermal flux efficiency since there will be essentially zero flux through the intact portions of the skin which still have the undisrupted stratum corneum layer and do not have a formed pathway open to the viable layers of the skin.

In use, a three-electrode assembly as described above can be operated according to a selective on-off cycling of the various electrode assemblies within the electro-osmotic pump assembly. For example, in a first electro-osmotic pump cycle, the electro-osmotic pump (EOP) can be activated by completing a circuit between the first and second electrode assemblies in order to create a relatively high concentration of the bioactive agent in the proximity of the microporous openings in the bottom surface of the delivery matrix. During a second electro-transport cycle, one or both of the first and second EOP electrode assemblies can be charged with the same polarity as the net charge on the particular bioactive agent to be transdermally delivered. The third electrode assembly, which can be positioned remotely from the delivery matrix and in communication with the surface of the skin, can then be operated as a counter electrode. In this electro-transport mode, the electro-repulsive force exerted on the bioactive agent can actively drive the bioactive agent into the micropores of the subject.

Of course, it should be appreciated that this electro-transport mode (ETM) and the electro-osmotic-pump mode (EOP) can be modulated in an on-off manner, or in any level between off and maximum intensity. By keeping the amount and duration of the ETM within certain exemplary limits, such as, for example, 10 ms on and 50 ms off, the average current which will flow through the skin tissues of a subject during ETM can be kept to a low enough level that any shifts in local pH can be neutralized during the off-time of the ETM by the normal micro-fluidic action within the skin tissues and the natural diffusion of ions when no electric field is present. As will be appreciated by one of skill in the art, this can work to establish uniform concentration of all mobile species, thus bringing the pH back to its normal physiological state. As such, this modulation of on-time to off-time of the ETM can also eliminate irritation due to a disruption of the normal pH of the skin tissues.

It should be understood that the specific duty cycles of the EOP mode or cycle and the ETM mode or cycle can depend on the particular permeant to be transdermally delivered and the current levels applied to both the EOP and ETM. Whereas a rough calculation can be made that will ensure the pH of the viable tissues stays within some predetermined boundary, in practice, these duty cycles can be determined experimentally by simply placing a small pH sensor under the patch to monitor the effects of different duty cycles. A further feature of this invention would be to incorporate a pH sensing element into the patch and use the output generated by it as a feedback signal to the system controller such that a closed-loop control circuit is implemented which ensures that the pH is held within the programmed boundaries, regardless of subject-to-subject variations in local skin physiology, environmental factors, or other forces which may affect the local environment.

Figure 6:
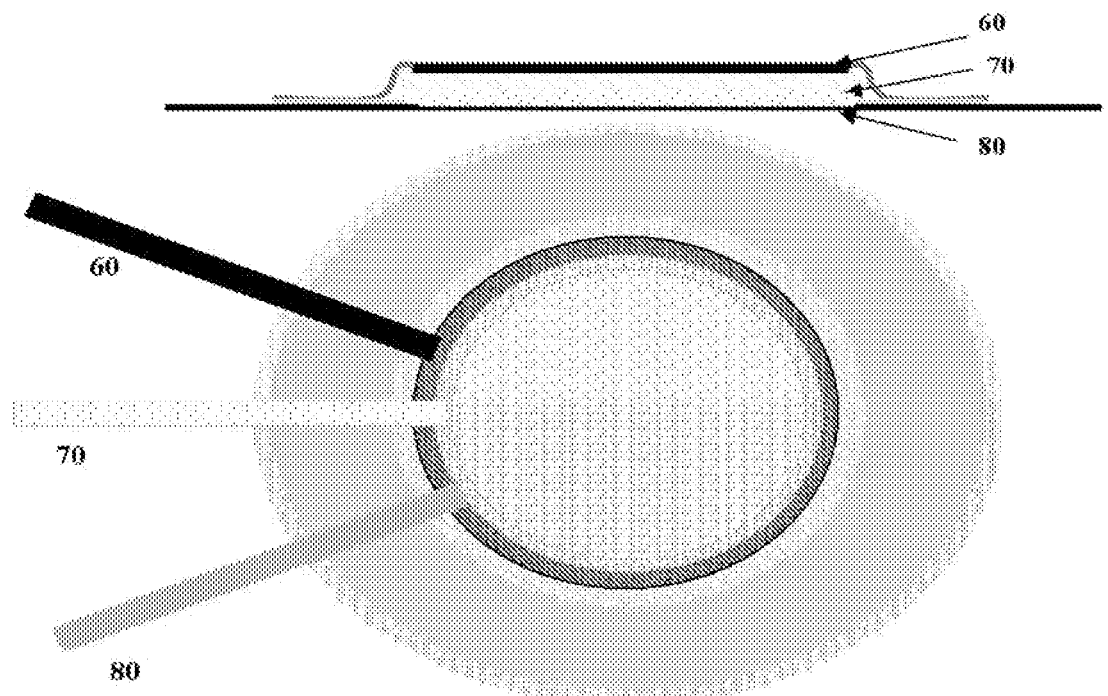
FIG. 6 illustrates an exemplary transdermal permeant delivery patch according to one aspect of the present invention where the patch assembly further comprises a first, second and third electrode assembly.

With reference to FIG. 6, an exemplary patch assembly further comprising a three-electrode osmotic pump assembly is depicted. As illustrated, the exemplary device comprises a transdermal patch assembly, comprising a microporated delivery matrix as previously described herein. The delivery matrix is constructed and arranged such that it has a top surface and an opposed bottom surface. A backing support layer, having an inwardly facing surface is at least partially connected to the top surface of the delivery matrix. The microporated delivery reservoir comprises a top surface and an opposed bottom surface. A first electrode assembly 60 is positioned in electrical communication with the top surface and a second electrode assembly 70 is positioned in electrical communication with the bottom surface. A third or counter electrode 80 is remotely positioned from the delivery matrix and adapted to be positioned in electrical communication with the skin of a subject. A complete circuit can then be created between at least any two of the first, second and third electrodes by placing at least two of the first, second and third electrode assemblies in selective or controllable electrical communication with a voltage or current source (not illustrated).

EXAMPLES

The following examples are put forth so as to provide those of ordinary skill in the art with a complete disclosure and description of how the devices, systems and methods claimed herein are made, performed and evaluated. These examples are intended to be purely exemplary of the invention and are not intended to limit the scope of what the inventors regard as their invention. Unless indicated otherwise, parts are parts by weight, temperature is degrees C. or is at ambient temperature, and pressure is at or near atmospheric.

Hydromorphone

Figure 7:
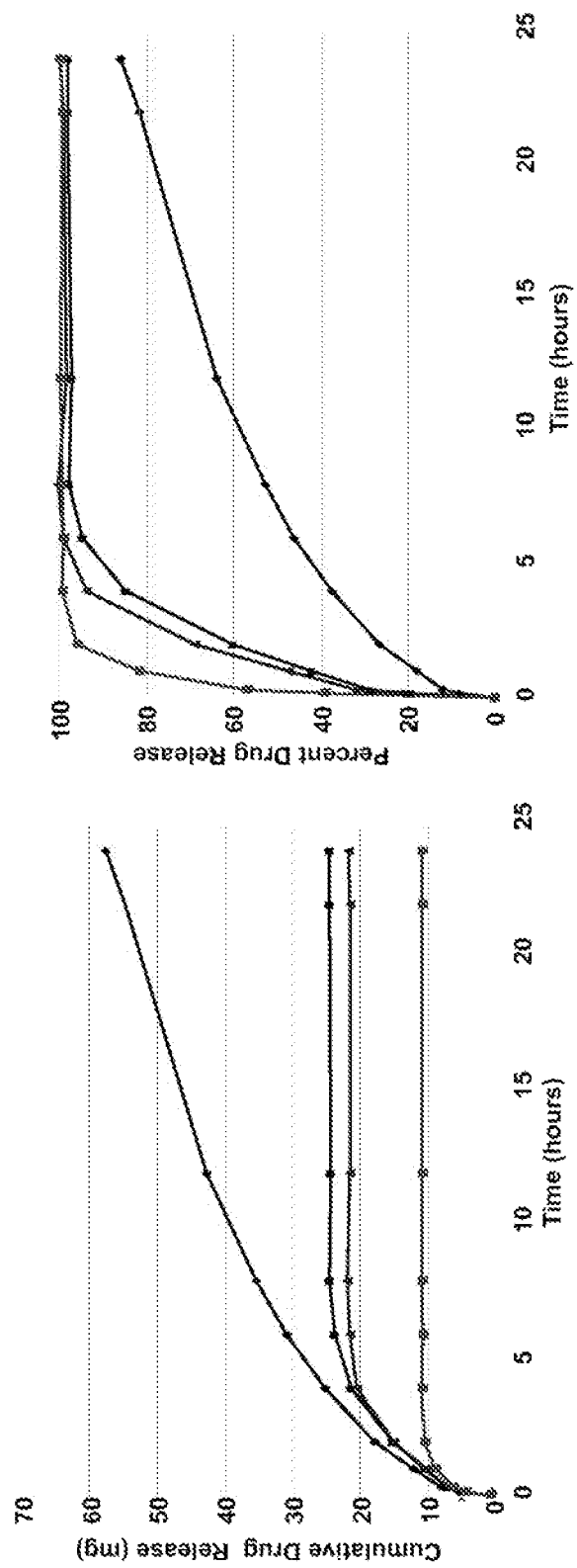
FIG. 7 is a chart reporting exemplary in vitro release kinetics for a permeant delivery reservoir of the present invention.

FIG. 7 reports the effect of permeant delivery patch thickness on the in vitro drug release kinetics for various permeant delivery patches of the present invention. Four permeant delivery patches were prepared according to the present invention. The four matrices each comprised ethylene vinyl acetate copolymer (EVA). The permeant formulations disposed within the EVA matrices comprised hydromorphone HCl (HM) as the bioactive agent and mannitol and propylene glycol (PG) as filler components and were approximately 1.44 cm in area. The first patch had a thickness of approximately 1.00 mm and comprised approximately 67 mg of hydromorphone. The second patch had a thickness of approximately 0.50 mm and comprised approximately 25 mg of hydromorphone HCl. The third patch had a thickness of approximately 0.44 mm and comprised approximately 22 mg of hydromorphone. The fourth patch had a thickness of approximately 0.22 mm and comprised approximately 11 mg of hydromorphone HCl.

In vitro tests using each of the four patches were conducted for an administration period of approximately 24 hours. Using conventional means for analysis, the cumulative hydromorphone HCl release and relative percentage of hydromorphone HCl release for each of the four permeant delivery patches over the 24-hour administration period are reported by the plots depicted in FIG. 7.

Figure 8:
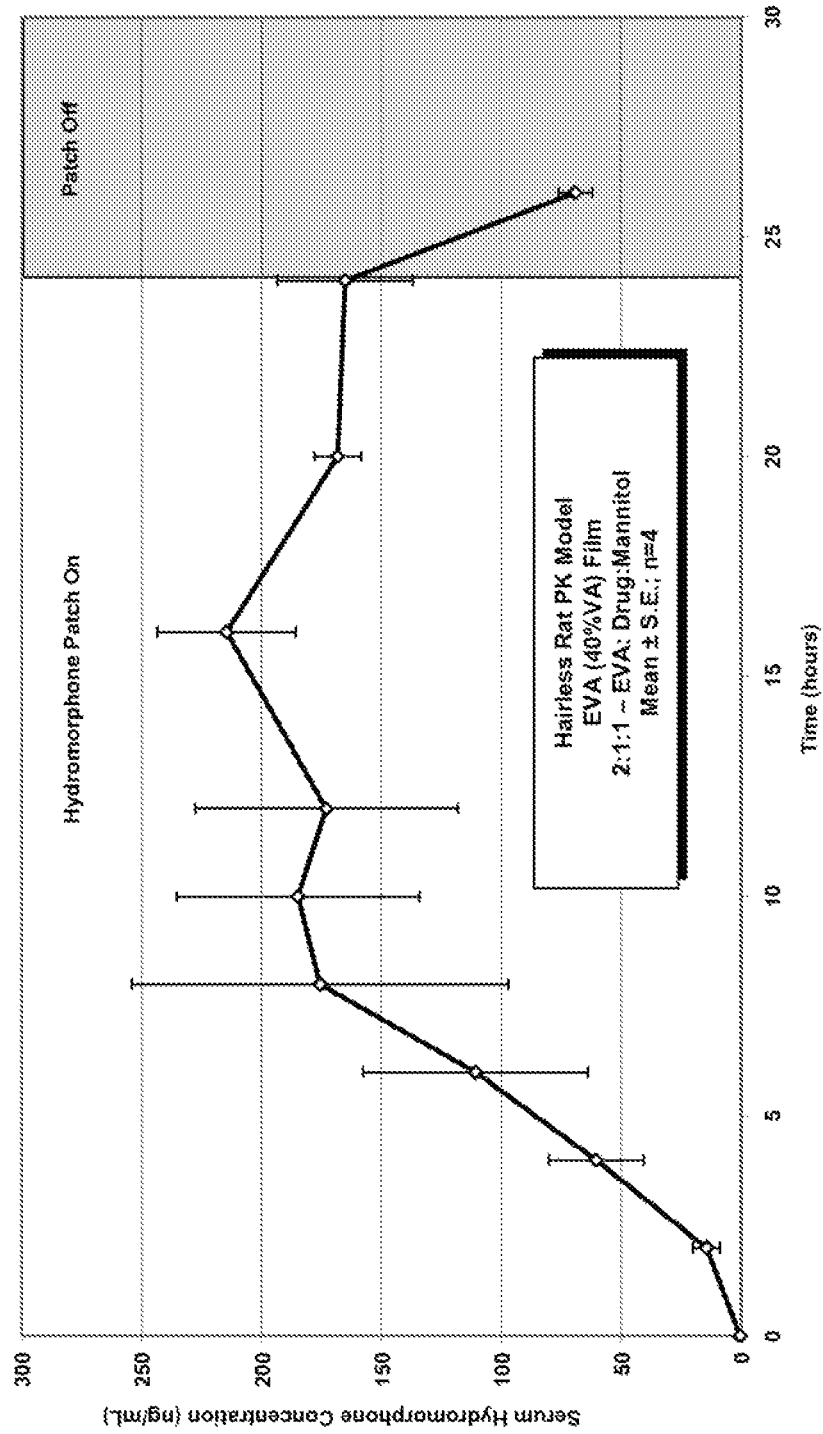
FIG. 8 is a chart reporting exemplary pharmacokinetic profile data for a permeant delivery reservoir or matrix according to one aspect of the present invention.

FIG. 8 reports the mean pharmacokinetic profile (PK profile) for an exemplary permeant delivery device according to the present invention that was tested on the abdomen region of four different hairless rat subjects. The permeant patch was a film having a thickness of approximately 1.4 millimeters and comprised 50 weight percent of an ethylene vinyl acetate copolymer having approximately 40% vinyl acetate component as the matrix material. The permeant composition comprised 25 weight percent hydromorphone HCl (relative to the total weight percent of the permeant patch) as the bioactive agent and 25 weight percent mannitol (relative to the total weight of the permeant patch) as additional filler component. The mean serum hydromorphone concentration in the hairless rats as a function of a 24-hour administration period is reported in FIG. 8.

Fentanyl Citrate

Figure 9:
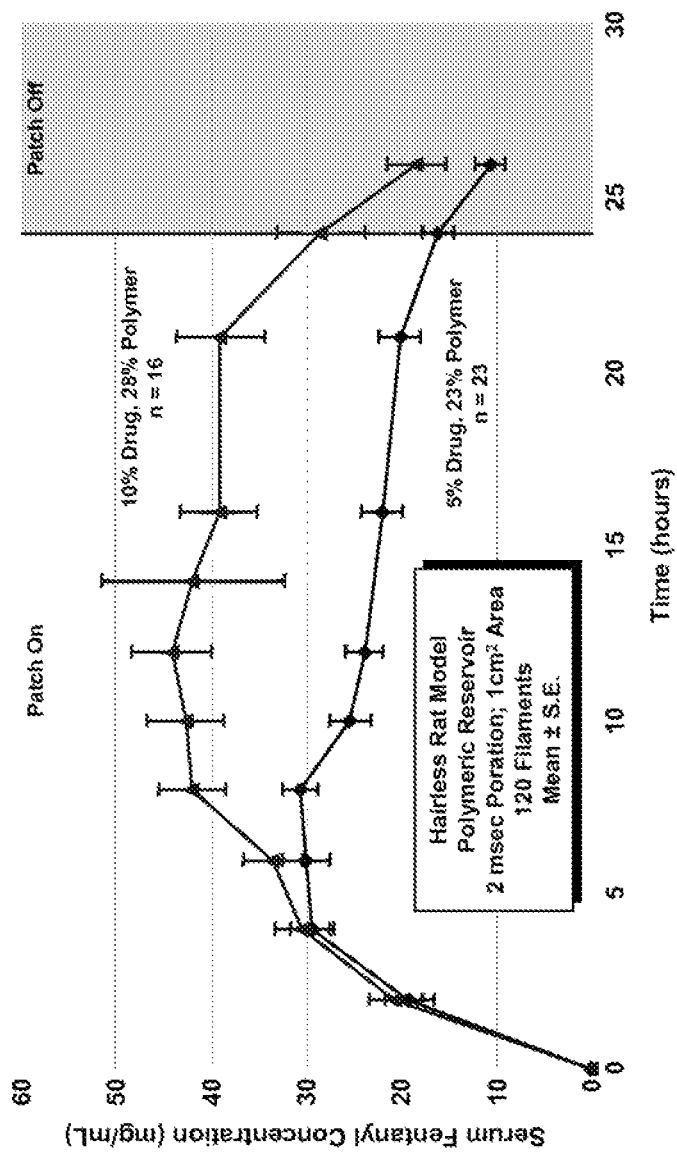
FIG. 9 reports the effects of changes in the polymer and fentanyl citrate loading on serum drug concentrations in the hairless rat for permeant delivery reservoirs according to the present invention.

FIG. 9 reports the mean fentanyl citrate serum level PK profile for permeant delivery patches of the present invention comprising differing concentrations of fentanyl citrate. In particular, shown is a comparison of mean fentanyl citrate serum level PK profiles for delivery patches prepared according to procedures similar to the following for 10% fentanyl citrate.

Preparation of an exemplary permeant delivery patch comprising 10% fentanyl citrate as the bioactive agent: To prepare the patch, mannitol is sieved using a 200 mesh sieve before use.

The patch can then be prepared by charging approximately 3000 mg of fentanyl citrate and approximately 18450 mg of mannitol into a vial and allowing the mixture to blend for at least 6 hours. Approximately 8550 mg of ethylene vinyl acetate comprised of approximately 40% vinyl acetate component can be added to the blended mix of fentanyl citrate and mannitol. The charged materials can be continuously stirred and heated in a temperature controlled container to a temperature in the range of approximately 80 C to 120 C. After the mixture achieves a dough-like consistency, the mixture can then be transferred to a backing film such as the Scotchpak backing available from 3M®.

Once deposited on the backing material, the dough-like material can be compressed between the backing layer and a protective release liner layer (such as the 1521 single-sided polyethylene film, also available from 3M®) to provide a patch having a desired thickness. After the patch material has cooled, the resulting film can then be cut to provide a patch having a surface area of, for example, approximately 1 cm$^2$. A patch prepared according to the foregoing procedure can, for example, comprise a concentration of bioactive agent of approximately 3.8 mg fentanyl citrate per patch. Prior to applying the exemplary patch onto a test subject, the protection release layer would first be removed to expose the bottom surface of the matrix.

FIG. 9 shows that, in one aspect of the present invention, fentanyl citrate can be delivered through micropores in the skin and that the steady-state level can be controlled by the fentanyl content of the delivery patch.

Fentanyl Chase For the fentanyl chase study, the abdomen of the hairless rat was again microporated followed by the application of a film or solution of interest. The patch (film or solution) was removed at predetermined specified times (i.e., 12 hours after application) and the administration site was covered with a subsequent or chase liquid reservoir patch, filled with about 200 uL of saturated fentanyl citrate solution. Blood samples were then removed from the tail vein of the hairless rat (typically 6-10 hours after patch change or 18-22 hours after microporation). Serum was separated from the blood samples for fentanyl analysis.

Figure 10:
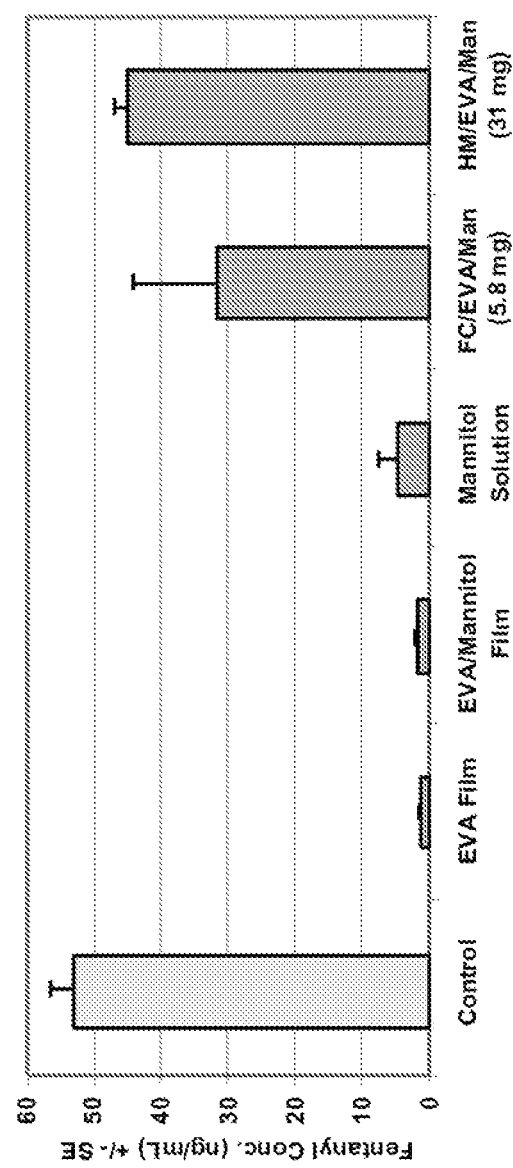
FIG. 10 reports fentanyl serum concentrations in the hairless rat after application of placebo or drug-containing films.

Data generated by such a fentanyl chase study is shown in FIG. 10. Twelve hours after application of one of the formulations (listed on the x-axis) the site was covered with a saturated fentanyl citrate solution and blood sampling commenced. The y-axis represents the average serum fentanyl levels reached 6-10 hours after application of the fentanyl solution. The control bar represents levels attained 6-10 hours after a saturated fentanyl citrate solution had been applied to freshly microporated skin. From the data it is apparent that by covering a freshly microporated site for 12 hours with a film made from solely EVA the delivery of fentanyl is prevented. The same approximate results were obtained if the site were covered with a film made from EVA/mannitol or if covered with a saturated mannitol solution. If, on the other hand, the site was first covered with a film containing fentanyl or hydromorphone, then fentanyl levels were observed at approximately 60% and 85% respectively of those obtained for the control.

Insulin

Figure 11:
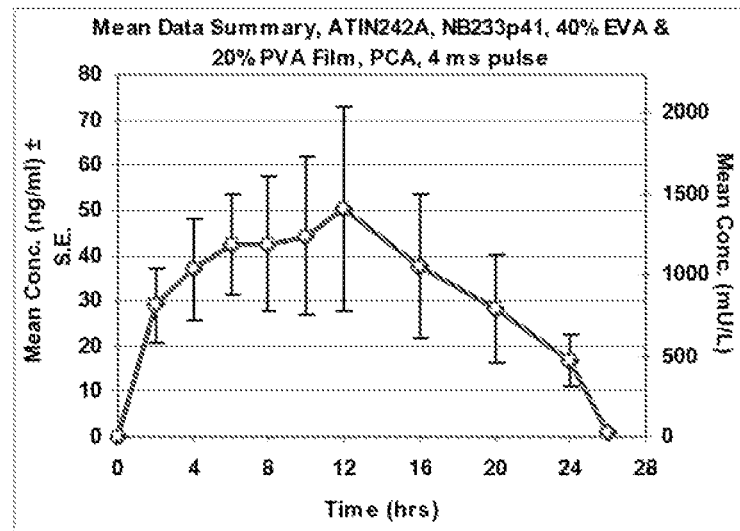
FIG. 11 is a chart demonstrating the effect of adding polyvinyl alcohol (PVA), a water-soluble polymer, to an insulin formulation containing tris as a permeability enhancer.

FIG. 11 reports a chart demonstrating the effect of adding polyvinyl alcohol (PVA), a water-soluble polymer, to an insulin formulation containing tris as a permeability enhancer. The addition of the polymer affords an extended profile of insulin delivery by controlling release of drug and/or permeability enhancer from the film. The matrix scaffold is comprised of ethylene vinyl acetate (EVA).

Figure 12:
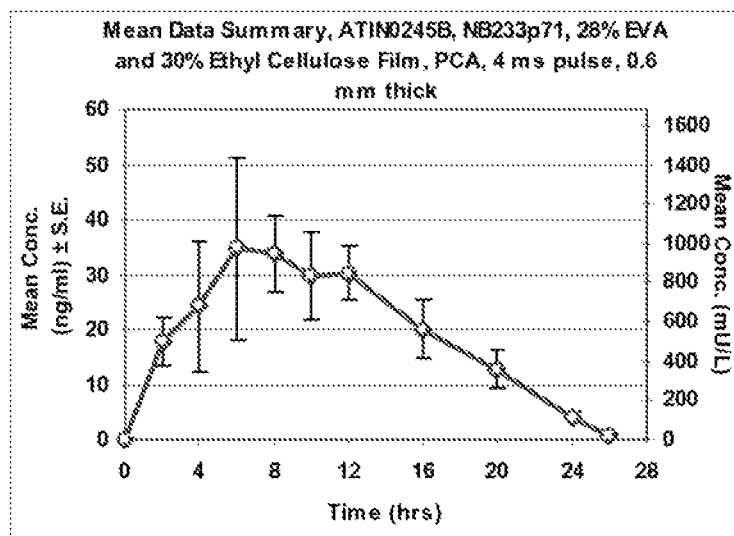
FIG. 12 is a chart demonstrating the effect of adding ethyl cellulose (EC), a water-insoluble polymer to an insulin formulation containing tris as a permeability enhancer.

FIG. 12 reports a chart demonstrating the effect of adding ethyl cellulose (EC), a water-insoluble polymer to an insulin formulation containing tris as a permeability enhancer. The addition of the polymer affords an extended profile of insulin delivery by controlling the release of drug and/or permeability enhancer from the film. The matrix scaffold is comprised of ethylene vinyl acetate (EVA).

Exenatide

Figure 13:
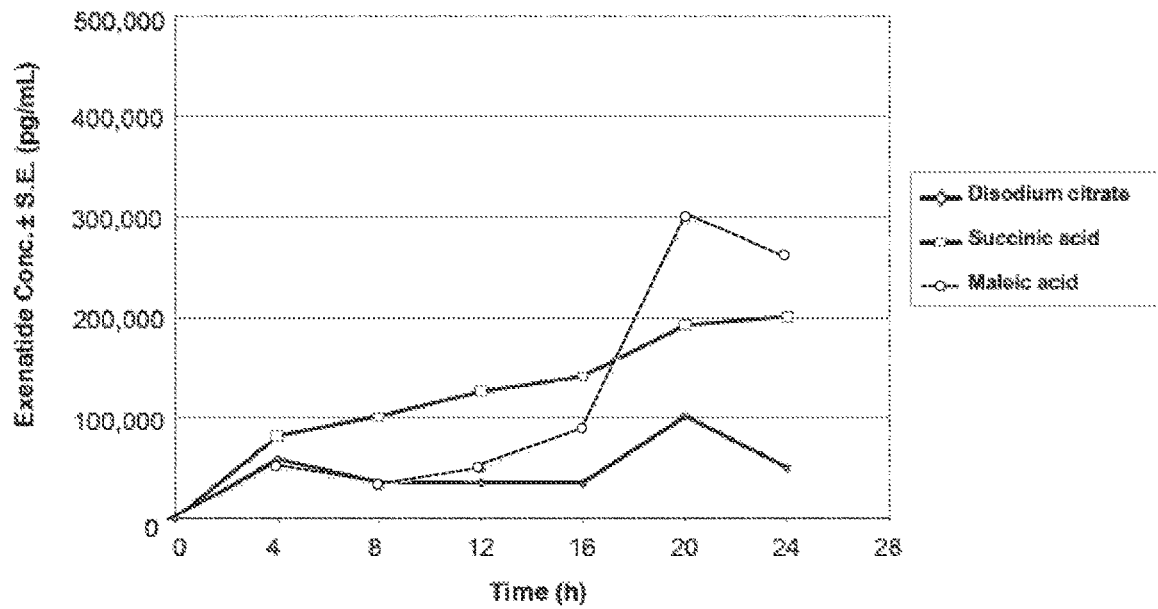
FIG. 13 is a chart demonstrating the effect of various permeability enhancers on exenatide delivery in the hairless rat.

FIG. 13 reports a chart demonstrating the effect of various permeability enhancers on exenatide delivery in the hairless rat. Animals were microporated on the abdomen and a patch containing a 20 OuL solution of exenatide (10.5 mg/mL) and the agent of interest (3% w/v) was applied over the site. A fresh solution was re-applied over the site every four hours and blood was sampled for exenatide levels over 24 hours. While disodium citrate provided roughly steady levels for the 24 hour period, the use of either succinic acid or maleic acid provided enhanced levels.

Figure 14:
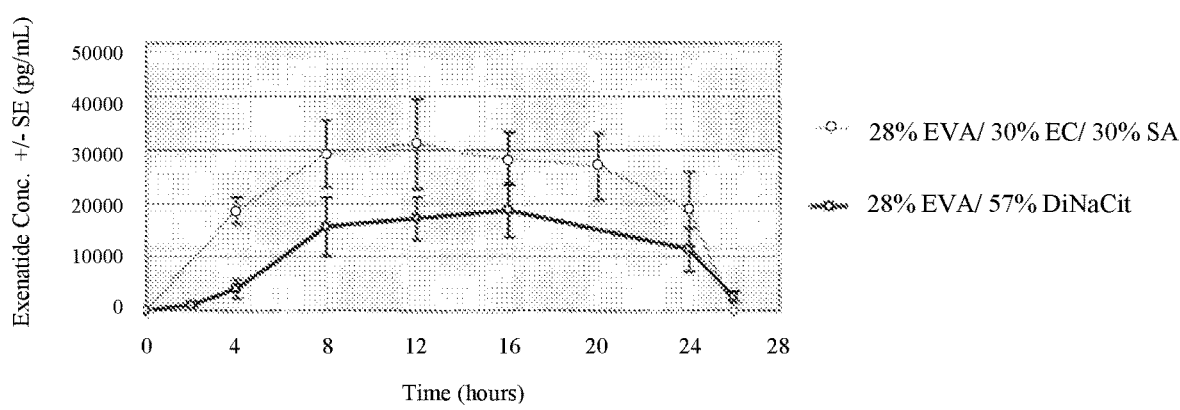
FIG. 14 is a chart demonstrating the effect of succinic acid (SA) and ethyl cellulose (EC) in a formulation designed to achieve extended delivery of exenatide over 24 hours.

FIG. 14 reports a chart demonstrating the effect of succinic acid (SA) and ethyl cellulose (EC) in a formulation designed to achieve extended delivery of exenatide over 24 hours. The 30% succinic acid formulation provides higher Cmax and area under the curve (AUC) relative to a formulation containing 57% disodium citrate (DiNaCitrate). The matrix scaffold is comprised of ethylene vinyl acetate (EVA).

Figure 15:
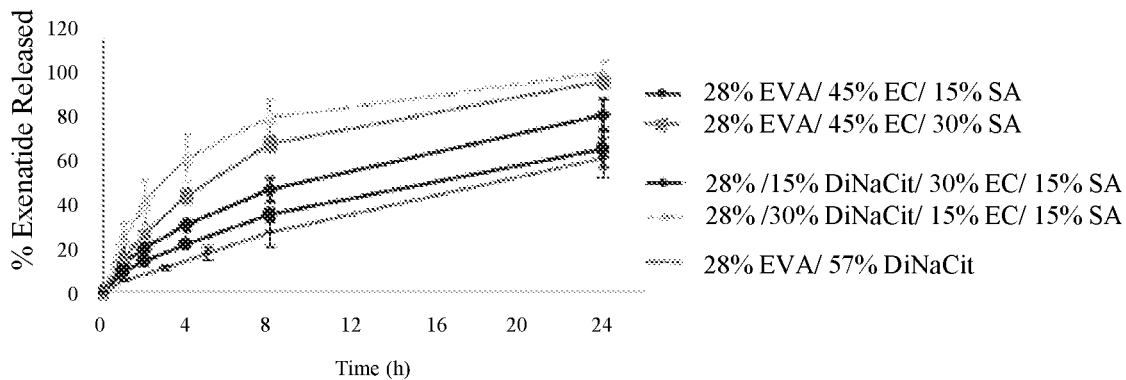
FIG. 15 shows the effect of ethyl cellulose to control exenatide release from succinic acid and disodium citrate films.

FIG. 15 reports a chart demonstrating the effect of polymer and/or permeability enhanceres on in vitro exenatide release. The identity or composition of the permeability enhancer can be modified to alter the dissolution profile of the films. For example, 30% ethyl cellulose-containing films release exenatide at a faster rate than 45% ethyl cellulose-containing films.

Figure 16:
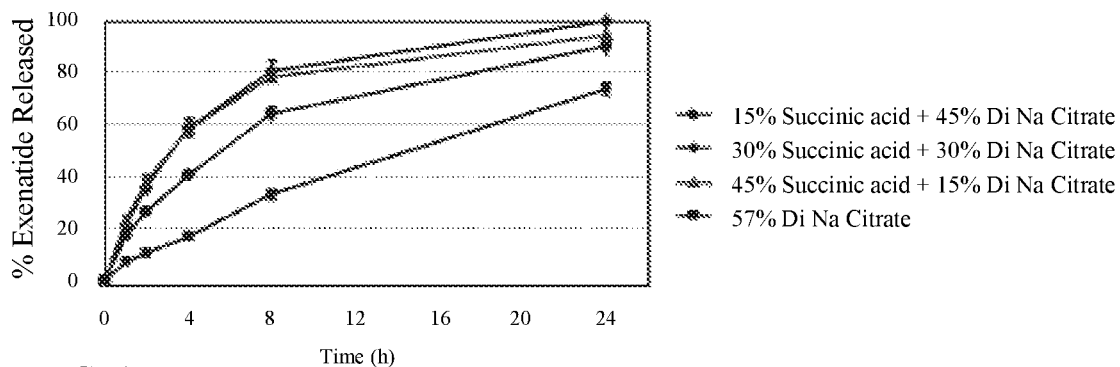
FIG. 16 is a chart demonstrating the effect of permeability enhancer composition on the in vitro release of exenatide from exenatide films containing ethylene vinyl acetate (EVA) and the permeability enhancers of interest.

FIG. 16 reports a chart demonstrating the effect of permeability enhancer composition on the in vitro release of exenatide from exenatide films containing ethylene vinyl acetate (EVA) and the permeability enhancers of interest. Increasing percentages of disodium citrate have the effect of slowing the rate of exenatide release from the films.

Pore Permeability Enhancers

Figure 17:
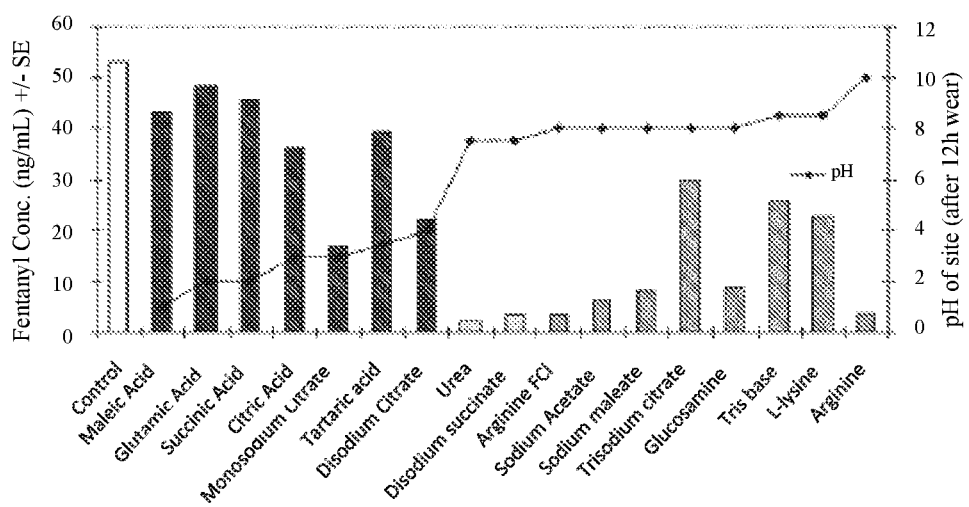
FIG. 17 shows the effect of permeability enhancer identity on the maintenance of pore permeability.

FIG. 17 reports the effect of permeability enhancer identity on the maintenance of pore permeability. Polymeric films were prepared with EVA and ~70% of the permeability enhancer listed. Hairless rats were microporated and the films were placed on the microporated site for 12 hours, after which time the polymeric film was replaced with a liquid reservoir patch containing a fentanyl citrate solution and blood fentanyl levels were monitored. In the absence of any permeability enhancer (i.e. films containing 100% EVA only) the fentanyl levels achieved after application of a fentanyl solution were <5 ng/mL, however, as shown, the inclusion of permeability enhancers produced significantly higher fentanyl levels. The pH of the skin at the site after final patch removal is shown for reference on the right axis. It is to be noted that this is simply one non-limiting example of a screening method for the effect of permeability enhancer identity on the maintenance of pore permeability. Other methods as well as other permeability enhancers may be used and tested.

What is claimed is:

1. A method for delivering a permeant through a biological membrane of a subject comprising:
    a) forming one or more micropores in the biological membrane; and
    b) placing a patch in physical contact with said one or more micropores, wherein said patch comprises:
        i) a matrix;
        ii) at least one hydrophilic permeant disposed within the matrix, wherein at least a portion of the hydrophilic permeant can dissolve in biological moisture received from the subject through said one or more micropores;
        iii) at least one permeability enhancer disposed within the matrix; and
        iv) at least one solubility control agent disposed within the matrix for controlling the dissolution of the hydrophilic permeant in the biological moisture received by the matrix to control delivery of the hydrophilic permeant into the subject via the at least one formed pathway, wherein the at least one solubility control agent comprises at least one selected from the group consisting of an agent that selectively controls pH of the biological moisture relative to the isoelectric point of the hydrophilic permeant, an agent that selectively controls the ionic strength of the biological moisture, and a salting-out agent.

2. The method of claim 1, wherein the one or more micropores are formed using at least one device from the group consisting of: thermal porators, mechanical porators, laser porators, and hydraulic porators.

3. The method of claim 1, wherein the one or more micropores are formed using a heat conducting element placed in substantial physical contact with the biological membrane to deliver sufficient energy to the biological membrane to thermally ablate said biological membrane.

4. The method of claim 1, wherein the one or more micropores are formed using a thin film tissue interface device.

5. The method of claim 1, wherein the hydrophilic permeant is a bioactive agent.

6. The method of claim 5, wherein the bioactive agent is a protein drug.

7. The method of claim 6, wherein the protein drug is exenatide.

8. The method of claim 6, wherein the protein drug is insulin.

9. The method of claim 5, wherein the bioactive agent is hydromorphone.

10. The method of claim 5, wherein the bioactive agent is fentanyl citrate.

11. The method of claim 5, wherein the bioactive agent is enoxaparin.

12. The method of claim 1, wherein the permeability enhancer is a pH control agent.

13. The method of claim 12, wherein the pH control agent is at least one selected from the group consisting of succinic acid, disodium citrate, trisodium citrate, and tris.

14. The method of claim 12, wherein the pH control agent is succinic acid.

15. The method of claim 12, wherein the pH control agent is disodium citrate.

16. The method of claim 1, wherein the matrix comprises at least one polymer.

17. The method of claim 16, wherein the polymer is a water insoluble polymer.

18. The method of claim 17, wherein the water insoluble polymer is at least one selected from the group consisting of: ethylene vinyl acetate and ethyl cellulose.

19. The method of claim 16, wherein the polymer is a water soluble polymer.

20. The method of claim 19, wherein the water soluble polymer is at least one selected from the group consisting of: polyethylene glycol, polyvinyl alcohol, and polyvinylpyrrolidone.

21. The method of claim 1, wherein the solubility control agent is at least one selected from the group consisting of: sodium citrate, sodium chloride and ammonium sulfate.

22. The method of claim 1, wherein the hydrophilic permeant is delivered to the subject for an administration period ranging from about 5 minutes to about 24 hours.

23. The method of claim 1, wherein the hydrophilic permeant is delivered to the subject for an administration period ranging from about 5 minutes to about 12 hours.

24. The method of claim 1, wherein the hydrophilic permeant is delivered to the subject as a bolus.

* * * * *

UNITED STATES PATENT AND TRADEMARK OFFICE
CERTIFICATE OF CORRECTION

PATENT NO. : 10,493,254 B2
APPLICATION NO. : 15/632329
DATED : December 3, 2019
INVENTOR(S) : Frank Tagliaferri et al.

Page 1 of 1

It is certified that error appears in the above-identified patent and that said Letters Patent is hereby corrected as shown below:

On the Title Page

Change Item (73) Assignee: delete "Nitto Denko Corporation, Tokyo (JP)" and replace with
--Passport Technologies, Inc., San Diego, California (US)--.

Signed and Sealed this
Twenty-fourth Day of November, 2020

Andrei Iancu
*Director of the United States Patent and Trademark Office*